US011483473B2

(12) United States Patent
Shiraki et al.

(10) Patent No.: US 11,483,473 B2
(45) Date of Patent: Oct. 25, 2022

(54) SURGICAL IMAGE PROCESSING APPARATUS, IMAGE PROCESSING METHOD, AND SURGERY SYSTEM

(71) Applicant: Sony Corporation, Tokyo (JP)

(72) Inventors: Hisakazu Shiraki, Kanagawa (JP); Takeshi Miyai, Kanagawa (JP); Kenji Takahashi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 58 days.

(21) Appl. No.: 16/496,452

(22) PCT Filed: Mar. 16, 2018

(86) PCT No.: PCT/JP2018/010391
§ 371 (c)(1),
(2) Date: Sep. 23, 2019

(87) PCT Pub. No.: WO2018/180573
PCT Pub. Date: Oct. 4, 2018

(65) Prior Publication Data
US 2021/0112197 A1    Apr. 15, 2021

(30) Foreign Application Priority Data
Mar. 31, 2017  (JP) .............................. JP2017-072244

(51) Int. Cl.
H04N 5/228 (2006.01)
H04N 5/232 (2006.01)
(Continued)

(52) U.S. Cl.
CPC ........... H04N 5/23229 (2013.01); G06F 8/65 (2013.01); G06T 7/0014 (2013.01); G06V 20/00 (2022.01);
(Continued)

(58) Field of Classification Search
CPC ............. H04N 5/23229; H04N 5/2624; H04N 5/2628; H04N 5/265; G16H 30/40; G06F 8/65; G06K 9/00624; G06T 7/0014
(Continued)

(56) References Cited

U.S. PATENT DOCUMENTS 6,750,890 B1 *  6/2004  Sugimoto ................. G06T 1/00
                                                345/594
2008/0058609 A1 *  3/2008  Garibaldi ............... G16H 40/63
                                                600/300
(Continued)

FOREIGN PATENT DOCUMENTS

CN   103188561 A   7/2013
CN   106464849 A   2/2017
(Continued)

OTHER PUBLICATIONS

Extended European Search Report dated Feb. 13, 2020 in European Patent Application No. 18774672.2, 7 pages.
(Continued)

Primary Examiner — Stephen P Coleman
(74) Attorney, Agent, or Firm — Xsensus LLP

(57) ABSTRACT

An image processing part applies an image process by software to a surgical region image, and a display control part controls a display of the surgical region image to which the image process is applied. The image processing part produces a pre-update processed image acquired by applying the image process established before updating the software to the surgical region image and a post-update processed image acquired by applying the image process established after updating the software to the surgical region image, and the display control part controls a display of at least a portion of at least either one of the pre-update processed image or the post-update processed image. The
(Continued)

present technique is applicable to a CCU of an endoscopic surgery system.

17 Claims, 16 Drawing Sheets

(51) Int. Cl.
  *G16H 30/40*  (2018.01)
  *G06F 8/65*  (2018.01)
  *G06T 7/00*  (2017.01)
  *H04N 5/262*  (2006.01)
  *H04N 5/265*  (2006.01)
  *G06V 20/00*  (2022.01)
  *G06F 3/04842*  (2022.01)
  *G06F 3/04845*  (2022.01)
  *H04N 5/225*  (2006.01)

(52) U.S. Cl.
  CPC ............ *G16H 30/40* (2018.01); *H04N 5/265* (2013.01); *H04N 5/2624* (2013.01); *H04N 5/2628* (2013.01); *G06F 3/04842* (2013.01); *G06F 3/04845* (2013.01); *G06F 2203/04803* (2013.01); *G06T 2200/24* (2013.01); *G06T 2207/10068* (2013.01); *G06T 2207/20081* (2013.01); *G06T 2207/20092* (2013.01); *G06T 2207/30168* (2013.01); *G06V 2201/03* (2022.01); *H04N 2005/2255* (2013.01)

(58) Field of Classification Search
  USPC ...................................... 348/222.1
  See application file for complete search history.

(56) References Cited

U.S. PATENT DOCUMENTS

| | | | |
|---|---|---|---|
| 2013/0174042 A1* | 7/2013 | Kim ........................ | G06F 8/65 715/735 |
| 2015/0085186 A1* | 3/2015 | Amling .................. | H04N 21/47 348/383 |
| 2016/0125575 A1* | 5/2016 | Takahashi ................ | G06T 5/50 382/275 |
| 2016/0249989 A1* | 9/2016 | Devam ................ | G09B 21/009 345/633 |
| 2017/0052757 A1* | 2/2017 | Kanda ...................... | G09G 5/14 |

FOREIGN PATENT DOCUMENTS

| | | |
|---|---|---|
| JP | 2002-176582 A | 6/2002 |
| JP | 2008-186294 A | 8/2008 |
| JP | 2009-226169 A | 10/2009 |
| JP | 2013-90194 A | 5/2013 |
| WO | 2006/093225 A1 | 9/2006 |
| WO | WO-2015105951 A1 | 7/2015 |

OTHER PUBLICATIONS

International Search Report and Written Opinion dated Jun. 5, 2018 for PCT/JP2018/010391 filed on Mar. 16, 2018, 10 pages including English Translation of the International Search Report.

* cited by examiner

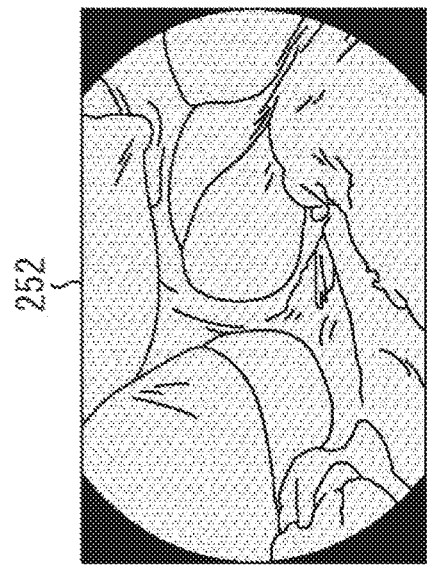
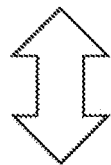
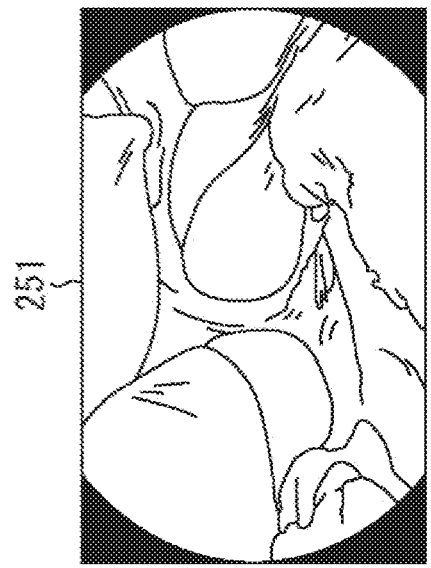
FIG. 6

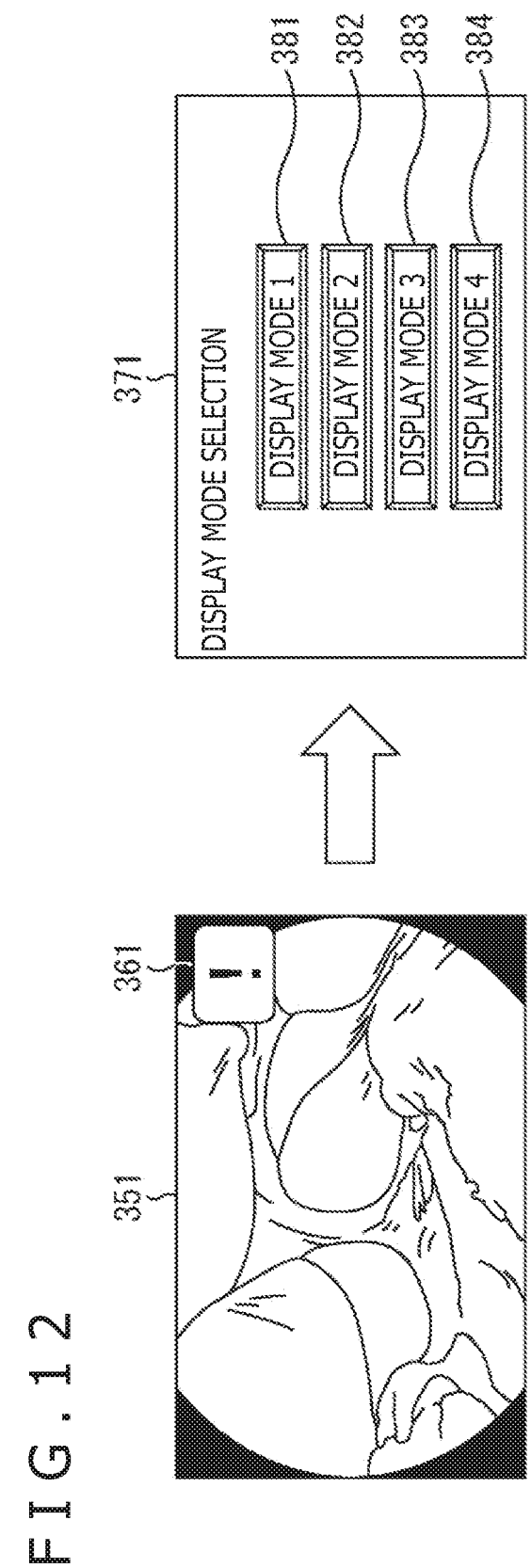
F I G . 12

SURGICAL IMAGE PROCESSING APPARATUS, IMAGE PROCESSING METHOD, AND SURGERY SYSTEM

CROSS-REFERENCE TO RELATED APPLICATIONS

The present application is based on PCT filing PCT/JP2018/010391, filed Mar. 16, 2018, which claims priority to JP 2017-072244, filed Mar. 31, 2017, the entire contents of each are incorporated herein by reference.

TECHNICAL FIELD

The present technique relates to a surgical image processing apparatus, an image processing method, and a surgery system, and more particularly to a surgical image processing apparatus, an image processing method, and a surgery system that each enable an easy comparison of images acquired before and after updating of software with each other.

BACKGROUND ART

In an endoscopic surgery system, various types of image processes are applied to a signal imaged by an endoscope. These image processes are realized by software, and a processor such as a GPU operates in accordance with a predetermined program and thereby executes these image processes.

PTL 1 discloses an endoscope system that executes maintenance such as updating of software through a communication line.

According to the above updating of the software, any updating of and any addition to the image processes can easily be executed.

CITATION LIST

Patent Literature

[PTL 1]
Japanese Patent Laid-Open No. 2009-226169

SUMMARY

Technical Problem

In the case where any updating of or any addition to the image processes is executed by the updating of the software, the image quality may, however, be varied between the images acquired before and after the updating of the software. In such a case, a doctor may desire to compare the image acquired before the variation of the image quality and the image acquired after the variation of the image quality with each other.

The present technique was conceived in view of the above circumstances and causes the images acquired before the updating of the software and acquired after the updating thereof to easily be compared with each other.

Solution to Problem

A surgical image processing apparatus of the present technique includes: an image processing part that applies an image process by software to a surgical region image; and a display control part that controls a display of the surgical region image to which the image process is applied, and the image processing part produces a pre-update processed image acquired by applying the image process established before updating the software to the surgical region image and a post-update processed image acquired by applying the image process established after updating the software to the surgical region image, and the display control part controls a display of at least a portion of at least either one of the pre-update processed image or the post-update processed image.

The surgical image processing apparatus can further have a difference computing part disposed therein that computes a difference between the pre-update processed image and the post-update processed image and, in a case where the difference is larger than a predetermined value, the display control part can be caused to control a display of information notifying of the case.

The surgical image processing apparatus can further have a scene detecting part disposed therein that detects a predetermined scene in the image and the display control part can be caused to display thereon one selected by a user, of the pre-update processed image and the post-update processed image for the detected scene.

The surgical image processing apparatus can further have a feature amount extracting part further disposed therein that extracts a feature amount of the detected scene, and a recording control part disposed therein that correlates the extracted feature amount and selection information indicating the one selected by the user of the pre-update processed image and the post-update processed image for the detected scene with each other and records the extracted feature amount and the selection information therein as history information.

The surgical image processing apparatus can further have a learning part disposed therein that learns which one of the pre-update processed image and the post-update processed image is selected by the user for the detected scene for each feature amount of the scene on the basis of the history information.

The surgical image processing apparatus can further have a referring part that refers to a learning result corresponding to the feature amount of a predetermined scene detected in another image, and the display control part can be caused to display thereon either the pre-update processed image or the post-update processed image for the predetermined scene in the other image on the basis of the referred learning result.

An image processing method of the present technique executed by a surgical image processing apparatus includes an image processing part that applies an image process by software to a surgical region image and a display control part that controls a display of the surgical region image to which the image process is applied, and the method includes steps of: producing a pre-update processed image acquired by applying the image process established before updating the software to the surgical region image and a post-update processed image acquired by applying the image process established after updating the software to the surgical region image; and controlling a display of at least a portion of at least either one of the pre-update processed image or the post-update processed image.

A surgery system of the present technique includes a surgical imaging apparatus that acquires a surgical region image, and a surgical image processing apparatus that includes an image processing part that applies an image process by software to the surgical region image and a display control part that controls a display of the surgical region image to which the image process is applied, and the image processing part produces a pre-update processed image acquired by applying the image process established before updating the software to the surgical region image and a post-update processed image acquired by applying the image process established after updating the software to the surgical region image and the display control part controls a display of at least a portion of at least either one of the pre-update processed image or the post-update processed image.

In the present technique, the pre-update processed image acquired by applying the image process established before updating the software to the surgical region image and the post-update processed image acquired by applying the image process established after updating the software to the surgical region image are produced, and the display of at least a portion of at least either one of the pre-update processed image or the post-update processed image is controlled.

Advantageous Effect of Invention

According to the present technique, an easy comparison between an image acquired before software updating and an image acquired after the software updating is enabled. The effect described above is not necessarily limited and any of the effects described herein may be achieved.

BRIEF DESCRIPTION OF DRAWINGS

FIG. 6 is a diagram depicting an exemplary display of the pre-update processed image and the post-update processed image.

FIG. 12 is a diagram depicting an exemplary display of the pre-update processed image and the post-update processed image.

DESCRIPTION OF EMBODIMENTS

Forms to implement the present disclosure (hereinafter, each referred to as "embodiment") will be described below. In addition, the description will be made in the following order.

1. Overview of Endoscopic Surgery System
2. Updating of Software
3. First Embodiment
4. Second Embodiment
5. Third Embodiment
6. Fourth Embodiment
7. Fifth Embodiment 1. Overview of Endoscopic Surgery System The overview of an endoscopic surgery system to which the present technique is applied will first be described.

Figure 1:
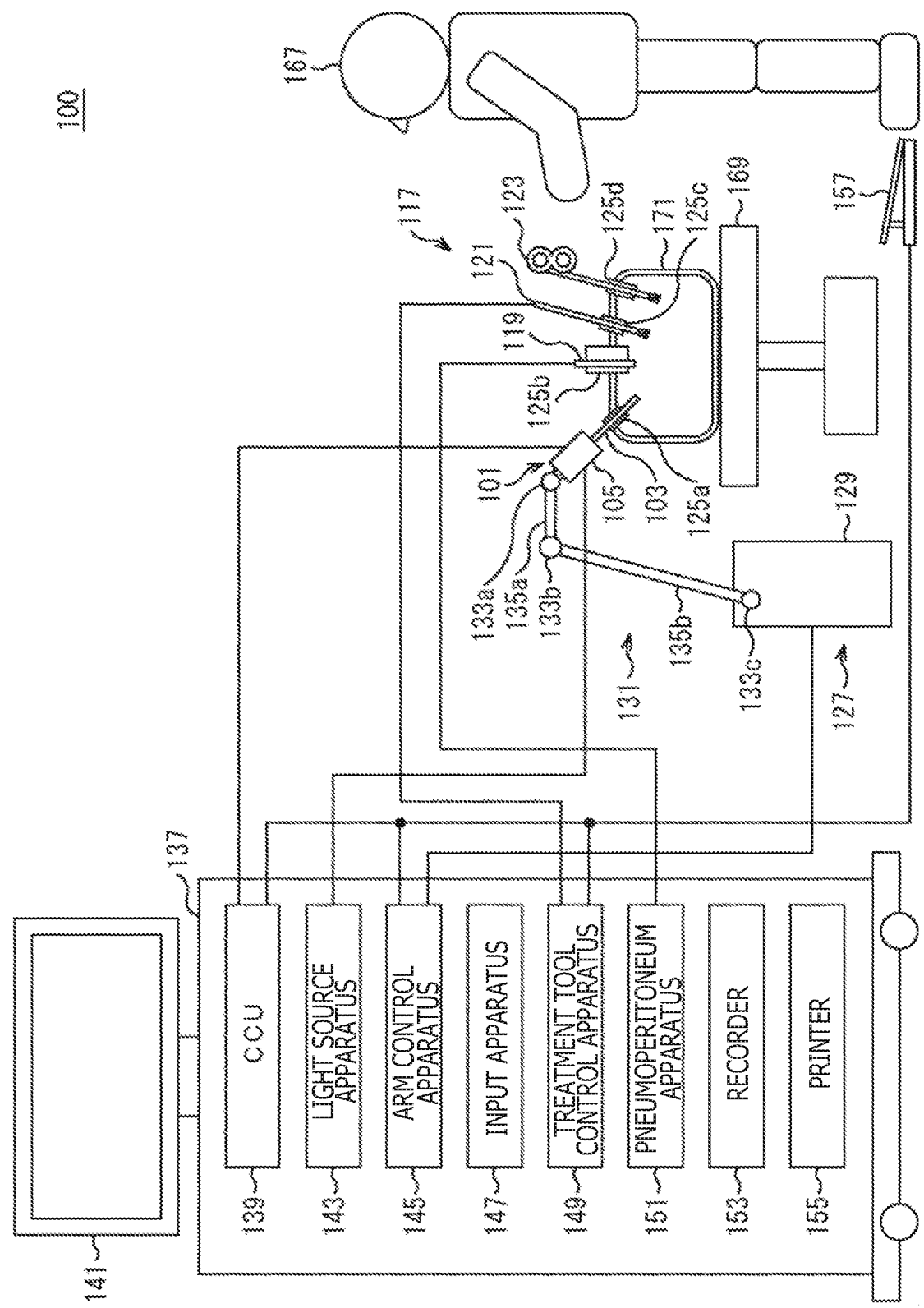
FIG. 1 is a diagram depicting an example of a schematic configuration of an endoscopic surgery system.

FIG. 1 is a diagram depicting an example of a schematic configuration of an endoscopic surgery system 100 to which the technique according to the present disclosure is applicable.

FIG. 1 depicts the state where an operator (a doctor) 167 performs a surgery for a patient 171 on a patient bed 169 using the endoscopic surgery system 100. The endoscopic surgery system 100 includes an endoscope 101, other surgical implements 117, a support arm apparatus 127 supporting the endoscope 101, and a cart 137 having various types of apparatuses for surgeries under the endoscope mounted thereon.

In a surgery under an endoscope, plural cylindrical-shape borers, each called "trocar," 125a to 125d are punctured into the abdominal wall instead of opening the abdomen by incising the abdominal wall. A lens barrel 103 of the endoscope 101 and the other surgical implements 117 are thereafter inserted into the body cavity of the patient 171 from the trocars 125a to 125d. In the example in FIG. 1, a pneumoperitoneum tube 119, an energy treatment tool 121, and forceps 123 are inserted in the body cavity of the patient 171 as the other surgical implements 117. The energy treatment tool 121 is a treatment tool that conducts incision and peeling off of a tissue, sealing of a blood vessel, or the like using a high-frequency current or an ultrasonic vibration. The depicted surgical implements 117 are, however, absolutely an example, and various types of surgical implements ordinarily used in a surgery under an endoscope such as, for example, tweezers and a retractor may be used as the surgical implements 117.

An image of the surgical region in the body cavity of the patient 171 imaged by the endoscope 101 is displayed on a displaying apparatus 141. The operator 167 performs a procedure such as, for example, incision of the affected area using the energy treatment tool 121 and the forceps 123, watching in real time the image of the surgical region displayed on the displaying apparatus 141. In addition, though not depicted, the pneumoperitoneum tube 119, the energy treatment tool 121, and the forceps 123 are held by the operator 167, an assistant, and the like during the surgery.

The support arm apparatus 127 includes an arm part 131 that extends from a base part 129. The arm part 131 includes joint parts 133*a*, 133*b*, and 133*c* and links 135*a* and 135*b*, and is driven by control of an arm control apparatus 145. The endoscope 101 is supported by the arm part 131, and the position and the posture thereof is controlled by the arm part 131. Stable fixation of the position of the endoscope 101 is thereby realized.

The endoscope 101 includes the lens barrel 103 whose region having a predetermined length from its tip is inserted into the body cavity of the patient 171, and the camera head 105 (an imaging apparatus) that is connected to the base end of the lens barrel 103. In the example in FIG. 1, the endoscope 101 is depicted that is configured as a what-is-called rigid scope including the rigid lens barrel 103 while the endoscope 101 may also be configured as a what-is-called flexible scope that includes the flexible lens barrel 103.

An opening into which an objective lens is fitted is disposed at the tip of the lens barrel 103. A light source apparatus 143 is connected to the endoscope 101, and a light beam produced by the light source apparatus 143 is guided to the tip of the lens barrel 103 by a light beam guide that extends into the inside of the lens barrel 103 and is applied toward the object to be observed in the body cavity of the patient 171 through the objective lens. In addition, the endoscope 101 may also be a forward viewing endoscope, or may be a forward-oblique viewing endoscope or a side viewing endoscope.

An optical system and an imaging element are disposed inside the camera head 105, and a reflected light beam (an observation light beam) from the object to be observed is condensed by the optical system onto the imaging element. The observation light beam is photo-electrically converted by the imaging element to produce an electric signal corresponding to the observation light beam, that is, an image signal corresponding to an observation image. The image signal is transmitted to a camera control unit (CCU) 139 as raw data. The camera head 105 is caused to mount thereon a function of adjusting the magnifying power and the focal length by properly driving the optical system.

In addition, to cope with, for example, stereoscopic viewing (3-D display), plural imaging elements may be disposed on the camera head 105. In this case, plural relaying optical systems are disposed inside the lens barrel 103 to guide the observation light beam to each of the plural imaging elements.

The cart 137 has various types of apparatuses mounted thereon.

The CCU 139 includes a CPU (central processing unit), a GPU (graphics processing unit), furthermore a GPGPU (general purpose computing on GPU), or the like, and generally controls the operations of the endoscope 101 and the displaying apparatus 141. More specifically, to the image signal received from the camera head 105, the CCU 139 applies various types of image processes to display the image based on the image signal such as, for example, a development process (a de-mosaic process). The CCU 139 provides the image signal to which the image process is applied, to the displaying apparatus 141. Moreover, the CCU 139 transmits a control signal to the camera head 105 to control its driving. The control signal may include information relating to the imaging condition such as the magnifying power and the focal length.

The displaying apparatus 141 displays thereon an image based on the image signal to which the image process is applied by the CCU 139 in accordance with the control from the CCU 139. In the case where the endoscope 101 supports imaging at a high resolution such as, for example, 4K (the number of the horizontal-direction pixels of 3,840× the number of the vertical-direction pixels of 2,160) or 8K (the number of the horizontal-direction pixels of 7,680× the number of the vertical-direction pixels of 4,320) and/or in the case where the endoscope 101 supports the 3-D display, the one capable of high-resolution displaying, and/or the one capable of 3-D displaying supporting each of the above may be used as the displaying apparatus 141. In the case where the displaying apparatus 141 supports high-resolution imaging such as that at 4K or 8K, an enhanced sense of immersion can be acquired by using a displaying apparatus having a size of 55 inches or larger as the displaying apparatus 141. Moreover, plural displaying apparatuses 141 having different definitions and different sizes may be disposed depending on the use.

The light source apparatus 143 includes a light source such as, for example, an LED (light emitting diode), and supplies an irradiation light beam used when the surgical region is imaged to the endoscope 101.

The arm control apparatus 145 includes a processor such as, for example, a CPU, and controls the driving of the arm part 131 of the support arm apparatus 127 in accordance with a predetermined control method by operating in accordance with a predetermined program.

An input apparatus 147 is an input interface for the endoscopic surgery system 100. A user can execute inputting of various types of information and inputting of an instruction into the endoscopic surgery system 100 through the input apparatus 147. For example, the user inputs various types of information relating to the surgery such as the body information of the patient, and information relating to the operative method of the surgery through the input apparatus 147. Moreover, for example, the user inputs an instruction to drive the arm part 131, an instruction to vary the conditions (such as the type of the irradiation light beam, the magnifying power, and the focal length) for the imaging by the endoscope 101, an instruction to drive the energy treatment tool 121, and the like through the input apparatus 147.

The type of the input apparatus 147 is not limited and the input apparatus 147 may be any type of known input apparatus. For example, a mouse, a keyboard, a touch panel, a switch, a foot switch 157, a lever, and/or the like are applicable as the input apparatus 147. In the case where the touch panel is used as the input apparatus 147, the touch panel may be disposed on the display face of the displaying apparatus 141.

Moreover, the input apparatus 147 may be a device to be attached to a user such as a spectacles-type wearable device or an HMD (head mounted display). In this case, various types of inputting are executed in accordance with any gesture or the line of sight of the user detected by each of these devices. Moreover, the input apparatus 147 may also include a camera capable of detecting any motion of the user to execute the various types of inputting in accordance with any gesture or the line of sight of the user detected from the video image imaged by the camera. Furthermore, the input apparatus 147 may also include a microphone capable of picking up a voice of the user to execute the various types of inputting using a sound through the microphone.

The input apparatus 147 is configured to be able to input various types of information in a non-contact manner as above and thereby, especially, the user (such as, for example, the operator 167) pertaining to a clean area can operate in a non-contact manner the devices pertaining to the non-clean area. Moreover, the user can also operate the devices without releasing his/her hands from the surgical implements held by the user, and thereby the convenience for the user is improved.

A treatment tool control apparatus 149 controls the driving of the energy treatment tool 121 for cauterization or incision of a tissue, sealing of a blood vessel, and the like. A pneumoperitoneum apparatus 151 feeds a gas into the body cavity of the patient 171 through a pneumoperitoneum tube 119 to inflate the body cavity thereof aiming at securing the visual field used by the endoscope 101 and securing a work space for the operator. A recorder 153 is an apparatus capable of recording various types of information relating to the surgery. A printer 155 is an apparatus capable of printing the various types of information relating to the surgery in various types of formats such as a text, an image, or a graph.

Figure 2:
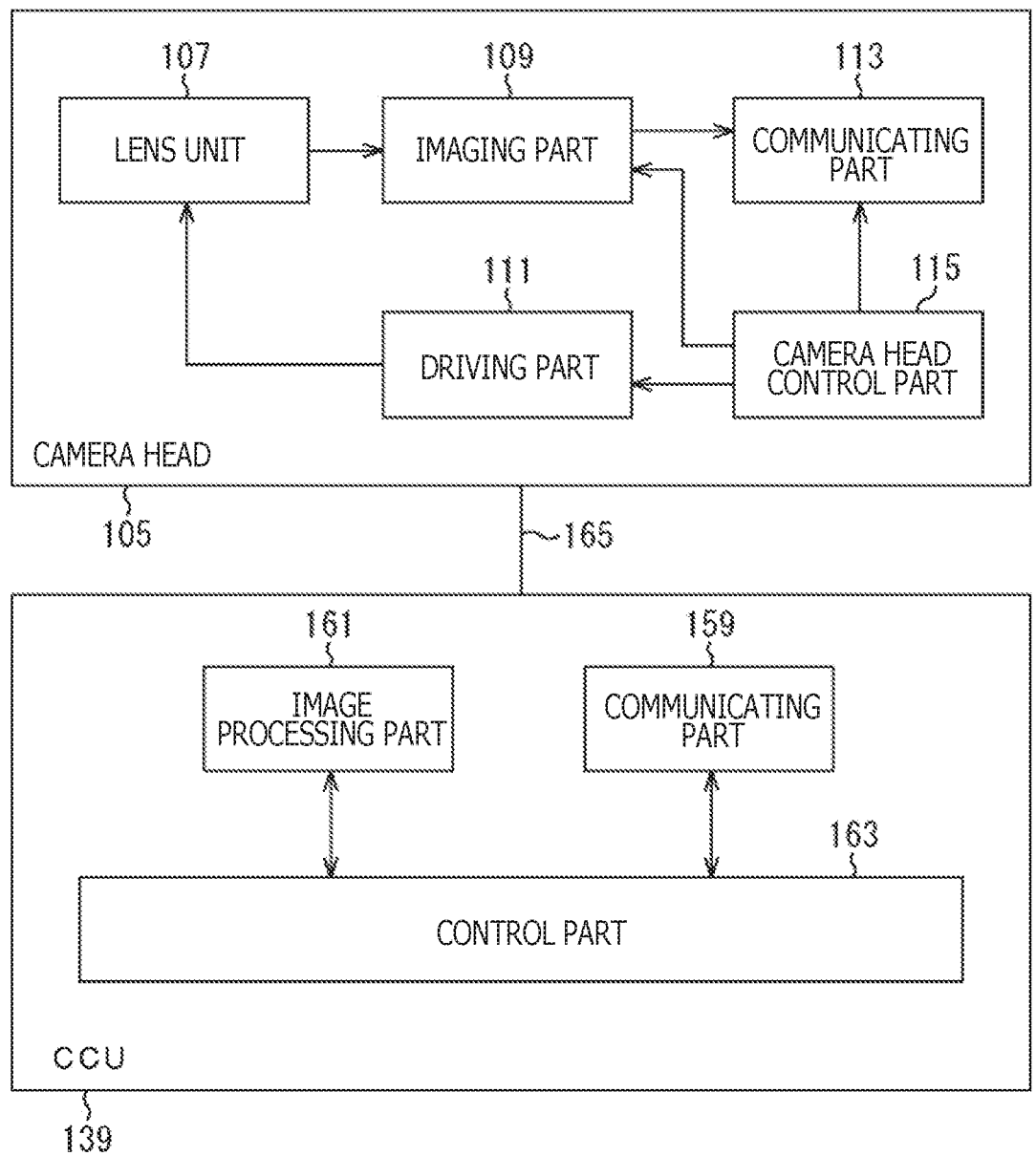
FIG. 2 is a block diagram depicting an example of the functional configurations of a camera head and a CCU.

Functions of the camera head 105 and the CCU 139 of the endoscope 101 will next be described in more detail with reference to FIG. 2. FIG. 2 is a block diagram depicting an example of the functional configurations of the camera head 105 and the CCU 139.

As depicted in FIG. 2, the camera head 105 includes as its functions a lens unit 107, an imaging part 109, a driving part 111, a communicating part 113, and a camera head control part 115. Moreover, the CCU 139 includes as its functions a communicating part 159, an image processing part 161, and a control part 163. The camera head 105 and the CCU 139 are bilaterally and communicably connected to each other by a transmission cable 165.

The functional configuration of the camera head 105 will first be described. The lens unit 107 is an optical system disposed in a connection part for the lens barrel 103. The observation light beam introduced from the tip of the lens barrel 103 is guided to the camera head 105 and enters into the lens unit 107. The lens unit 107 is constituted by a combination pf plural lenses including a zoom lens and a focusing lens. The lens unit 107 has its optical property adjusted such that the observation light beam is condensed on the light-receiving face of the imaging element of the imaging part 109. Moreover, the zoom lens and the focusing lens are configured to be movable as to their positions on the optical axis for adjustment of the scale factor and the focal point of the imaged image.

The imaging part 109 includes an imaging element and is arranged in the post-stage of the lens unit 107. The observation light beam already passing through the lens unit 107 is condensed on the light-receiving face of the imaging element and an image signal corresponding to an observed image is produced by photo-electric conversion. The image signal produced by the imaging part 109 is provided to the communicating part 113.

An imaging element capable of color-imaging that has the Bayer arrangement such as, for example, a CMOS (complementary metal oxide semiconductor) image sensor is used as the imaging element constituting the imaging part 109. In addition, an imaging element capable of supporting the imaging of an image at a high resolution such as, for example, 4K or higher may be used as the imaging element. Because the image of the surgical region can be acquired at a high resolution, the operator 167 can understand the state of the surgical region in detail and can therefore more smoothly progress the surgery.

Moreover, the imaging element constituting the imaging part 109 can be adapted to include a pair of imaging elements to respectively acquire image signals for the right eye and the left eye that correspond to the 3-D display. Executing the 3-D display enables the operator 167 to more accurately understand the depth of each of the in-vivo tissues in the surgical region. In addition, in the case where the imaging part 109 is constituted in a multi-plate form, plural systems each for the lens unit 107 are also disposed corresponding to the imaging elements.

Moreover, the imaging part 109 may not necessarily be disposed on the camera head 105. For example, the imaging part 109 may be disposed immediately after the objective lens inside the lens barrel 103.

The driving part 111 includes an actuator and moves the zoom lens and the focusing lens of the lens unit 107 along the optical axis by a predetermined distance in accordance with the control from the camera head control part 115. The scale factor and the focal point of the imaged image by the imaging part 109 can thereby be properly adjusted.

The communicating part 113 includes a communicating apparatus to transmit and receive various types of information to/from the CCU 139. The communicating part 113 transmits the image signal acquired from the imaging part 109 as raw data to the CCU 139 through the transmission cable 165. At this time, to display the imaged image of the surgical region with a low latency, it is preferred that the image signal be transmitted using optical communication. This is because, during the surgery, the operator 167 performs the surgery observing the state of the surgical region using the imaged image and it is therefore required that a moving image of the surgical region is displayed in real time as far as possible for the surgery to be safer and more reliable. In the case where the optical communication is executed, a photo-electric converting module converting an electric signal into an optical signal is disposed in the communicating part 113. The image signal is converted by the photo-electric converting module into an optical signal and is thereafter transmitted to the CCU 139 through the transmission cable 165.

Moreover, the communicating part 113 receives a control signal to control the driving of the camera head 105, from the CCU 139. The control signal includes information relating to the imaging conditions such as, for example, information to designate the frame rate of the imaged image, information to designate the exposure value for imaging, and/or information to designate the scale factor and the focal point of the imaged image. The communicating part 113 provides the received control signal to the camera head control part 115. In addition, the control signal from the CCU 139 may also be transmitted using the optical communication. In this case, a photo-electric converting module converting an optical signal into an electric signal is disposed in the communicating part 113, and the control signal is converted by the photo-electric converting module into an electric signal and is thereafter provided to the camera head control part 115.

In addition, the above imaging conditions such as the frame rate, the exposure value, the magnifying power, and the focal point are automatically set by the control part 163 of the CCU 139 on the basis of the acquired image signal. In short, a what-is-called AE (automatic exposure) function, a what-is-called AF (automatic focusing) function, and a what-is-called AWB (automatic white balance) function are mounted on the endoscope 101.

The camera head control part 115 controls the driving of the camera head 105 on the basis of the control signal from the CCU 139 received through the communicating part 113. For example, the camera head control part 115 controls the driving of the imaging element of the imaging part 109 on the basis of information to designate the frame rate of the imaged image and/or information to designate the exposure for the imaging. Moreover, for example, the camera head control part 115 properly moves the zoom lens and the focusing lens of the lens unit 107 through the driving part 111 on the basis of the information to designate the magnifying power and the focal point of the imaged image. The camera head control part 115 may further include a function of storing therein information to identify each of the lens barrel 103 and the camera head 105.

In addition, a tolerance property against any autoclave sterilization process can be imparted to the camera head 105 by arranging the configurations such as the lens unit 107 and the imaging part 109 in a sealed structure whose airtightness and waterproof property are high.

The functional configuration of the CCU 139 will next be described. The communicating part 159 includes a communicating apparatus to transmit and receive various types of information to/from the camera head 105. The communicating part 159 receives the image signal transmitted from the camera head 105 through the transmission cable 165. Concerning this, the image signal is advantageously enabled to also be transmitted using optical communication as above. In this case, supporting the optical communication, the communicating part 159 has the photo-electric converting module disposed therein that converts an optical signal into an electric signal. The communicating part 159 provides the image signal converted into an electric signal to the image processing part 161.

Moreover, the communicating part 159 transmits the control signal to control the driving of the camera head 105 to the camera head 105. The control signal may also be transmitted using the optical communication.

The image processing part 161 applies various types of image processes to the image signal that is the raw data transmitted from the camera head 105. The image processes include various types of known signal processes such as, for example, a development process, an image quality improvement process (a band emphasis process, a super resolution process, an NR (noise reduction) process, a camera shake correction process, and/or the like), and/or an enlargement process (an electronic zoom process). Moreover, the image processing part 161 executes a detection process for the image signal to execute the AE, the AF, and the AWB.

The image processing part 161 includes a processor such as a CPU, a GPU, or a GPGPU, and the above-described image processes and the detection process are executed by the fact that the processor operates in accordance with a predetermined program. In addition, in the case where the image processing part 161 includes plural GPUs, the image processing part 161 properly divides the information relating to the image signal and executes the image processes in parallel to each other using these plural GPUs.

The control part 163 executes various types of control relating to the imaging of the surgical region by the endoscope 101 and the display of the imaged image thereof. For example, the control part 163 produces the control signal to control the driving of the camera head 105. Concerning this, in the case where the imaging conditions are already input by the user, the control part 163 produces the control signal on the basis of the input by the user. Moreover, in the case where the AE function, the AF function, and the AWB function are mounted on the endoscope 101, the control part 163 properly calculates the optimal exposure value, the optimal focal distance, and the optimal white balance in accordance with the result of the detection process executed by the image processing part 161 and thereby produces the control signal.

Moreover, the control part 163 causes the displaying apparatus 141 to display thereon the image of the surgical region on the basis of the image signal to which the image process is applied by the image processing part 161. At this time, the control part 163 recognizes various types of objects in the surgical region image using various types of image recognition techniques. For example, the control part 163 can recognize the surgical implements 117 such as the forceps 123, specific in-vivo regions, any bleeding, the mist produced during the use of the energy treatment tool 121, and the like by detecting the shape of the edge and the color of each of the objects included in the surgical region image. When the control part 163 causes the displaying apparatus 141 to display thereon the image of the surgical region, the control part 163 causes the displaying apparatus 141 to display thereon various types of surgery support information superimposing this information on the image of the surgical region using the result of the recognition. The surgery support information is displayed being superimposed, to be presented to the operator 167 and the surgery can thereby be more safely and more reliably progressed.

The transmission cable 165 connecting the camera head 105 and the CCU 139 to each other is an electric signal cable supporting communication of any electric signal, an optical fiber supporting the optical communication, or a composite cable of these.

The communication is executed by wire using the transmission cable 165 in this example while the communication between the camera head 105 and the CCU 139 may be executed wirelessly. In the case where the communication between these two is executed wirelessly, the transmission cable 165 does not need to be run on the floor in the surgery room and the situation can therefore be resolved where any move of the medical staff members in the surgery room is obstructed by the transmission cable 165.

2. Updating of Software

Relating to the above, in the above-described endoscopic surgery system, the various types of image processes are applied to the image imaged by the endoscope. These image processes are realized by software and these image processes are executed by the fact that the processor such as a GPU operates in accordance with the predetermined program.

According to the update of the software (SW), any update of and any addition to the image processes can easily be executed.

On the other hand, in the case where any update of or any addition to the image processes is executed by updating the SW, the image quality of the image may be varied between those before the update and after the update. In such a case, the doctor may desire to compare the image before its image quality is varied and the image after its image quality is varied with each other. Furthermore, a risk is also present that such variation of the image quality influences the diagnosis and operation of the surgical implements by the doctor during the surgery.

For example, in the case where any update of SW to add thereto a camera shake correction process is executed, the image of the surgical region is stabilized and the visibility thereof is improved in many situations.

On the other hand, in the situation of peeling off or the like where a quick operation of the surgical implements is required, the latency from the imaging to the displaying is increased due to the camera shaking correction process and the operation of the surgical implements may look to be delayed. Moreover, the resolution may be somewhat degraded due to geometric transformation such as affine transformation, and micro tissues such as blood vessels and nerves may thereby be difficult to be seen.

Moreover, in the case where an update of the SW to add thereto a gray level correction process is executed, the visibility can be improved for a low gray-level portion in which the light beam from the light source is difficult to arrive. The contrast is, however, degraded in the portion having an intermediate gray level and the micro tissues such as blood vessels and nerves may be difficult to be seen.

Furthermore, in the case where an update of the SW to add thereto a structure emphasis process is executed, the micro tissues such as blood vessels and nerves are displayed being emphasized and the visibility of the portion can thereby be improved while this portion may also be difficult to be seen depending on the case.

In the case where the surgical region becomes difficult to be seen by the execution of the update of the SW as above, the operator also needs the image acquired before the update of the SW is executed.

Therefore, an embodiment will be described below, that enables an easy comparison between images acquired before updating the SW and after updating the SW with each other even after updating the SW, and that furthermore can avoid any risk of influencing the diagnosis and the operation of the surgical implements by the doctor during the surgery.

3. First Embodiment (Exemplary Configuration of Image Processing Apparatus)

An exemplary configuration of an image processing apparatus of a first embodiment according to the present technique will first be described with reference to FIG. 3.

Figure 3:
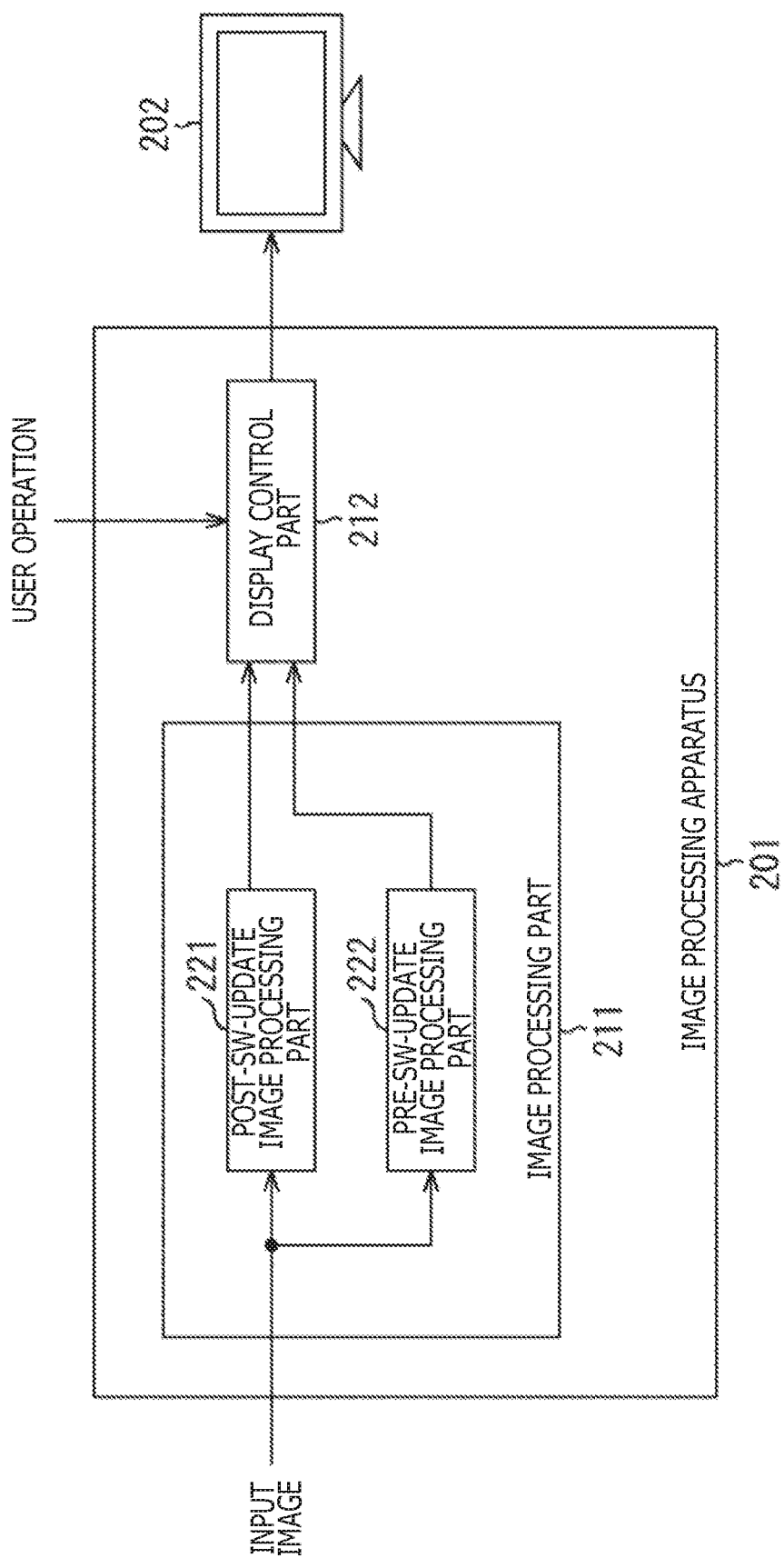
FIG. 3 is a block diagram depicting an exemplary functional configuration of an image processing apparatus of a first embodiment.

The image processing apparatus 201 in FIG. 3 corresponds to the above-described CCU 139, and applies image processes to, for example, the image signal of the surgical region image input from the camera head 105 (the input image) and outputs the result thereof to a displaying apparatus 202.

The displaying apparatus 202 corresponds to the above-described displaying apparatus 141, and displays thereon an image on the basis of the image signal output from the image processing apparatus 201.

The image processing apparatus 201 includes an image processing part 211 and a display control part 212.

The image processing part 211 corresponds to the above-described image processing part 161, and applies various types of image processes to the image signal of the input image. These image processes are realized by software (SW), and a processor such as a GPU operates in accordance with a predetermined program and thereby executes these image processes.

The SW realizing these image processes is updated by, for example, the fact that the predetermined program is installed from a recording medium. In addition, such a program may be installed through a network such as the Internet.

The image processing part 211 includes a post-SW-update image processing part 221 and a pre-SW-update image processing part 222.

The post-SW-update image processing part 221 outputs an image signal of a post-update processed image acquired by applying an image process established after updating the SW, that is, an image process realized by the SW of the latest-version to the input image.

The pre-SW-update image processing part 222 outputs an image signal of a pre-update processed image acquired by applying an image process established before updating the SW, that is, an image process realized by the SW of the immediately previous version to the input image.

In the case where the post-SW-update image processing part 221 and the pre-SW-update image processing part 222 are constituted by two GPU, the post-SW-update image processing part 221 and the pre-SW-update image processing part 222 can execute the image process established after updating the SW and the image process established before updating the SW in parallel to each other, that is, concurrently.

Moreover, the post-SW-update image processing part 221 and the pre-SW-update image processing part 222 can also be constituted by one GPU to serially execute the image process established after updating the SW and the image process established before updating the SW.

The display control part 212 causes the displaying apparatus 202 to display thereon at least a portion of at least either one of the post-update processed image or the pre-update processed image on the basis of the image signal output from the image processing part 211 (the post-SW-update image processing part 221 and the pre-SW-update image processing part 222). Moreover, the display control part 212 controls the display of the post-update processed image and the pre-update processed image on the displaying apparatus 202 in accordance with the operation of the user.

(Flow of Surgical Region Image Display Process)

Figure 4:
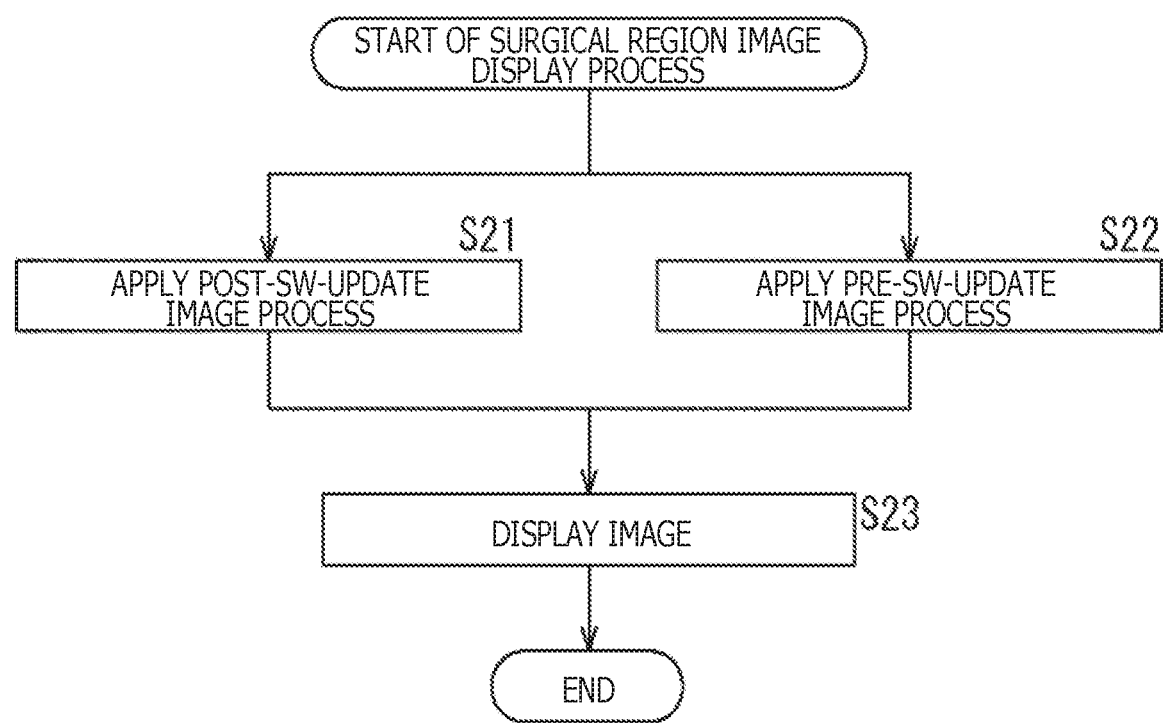
FIG. 4 is a flowchart explaining a surgical region image display process.

A flow of the surgical region image display process executed by the image processing apparatus 201 will next be described with reference to FIG. 4. The processes in FIG. 4 are started when a surgical region image acquired by imaging the surgical region (a moving image) is input into the image processing apparatus 201 from the endoscope 101 (the camera head 105).

At step S21, the post-SW-update image processing part 221 applies the image process established after updating the SW (the image process realized by the SW of the latest version) to the input surgical region image.

At step S22, the pre-SW-update image processing part 222 applies the image process established before updating the SW (the image process realized by the SW of the immediately previous version) to the input surgical region image.

It is assumed that the processes at steps S21 and S22 are concurrently executed in parallel to each other while these processes may serially be executed as described above. The image signal of the post-update processed image to which the image process established after updating the SW is applied and the image signal of the pre-update processed image to which the image process established before updating the SW is applied are output to the display control part 212.

At step S23, the display control part 212 causes the displaying apparatus 202 to display thereon the post-update processed image and the pre-update processed image on the basis of the image signals output from the post-SW-update image processing part 221 and the pre-SW-update image processing part 222.

According to the above processes, the image acquired after the image quality is varied by the update of the SW and the image acquired before the image quality is varied thereby are displayed as the images of the surgical region imaged by the endoscope 101 and the operator performing the surgery using the endoscope 101 can therefore easily compare these images with each other. As a result, the possibility can be reduced that the variation of the image caused by the update of the SW influences the diagnosis and the operation of the surgical implements by the doctor during the surgery.

Concerning the above, an exemplary display of the post-update processed image and the pre-update processed image that are displayed on the displaying apparatus 202 will be described.

(Exemplary Display 1)

Figure 5:
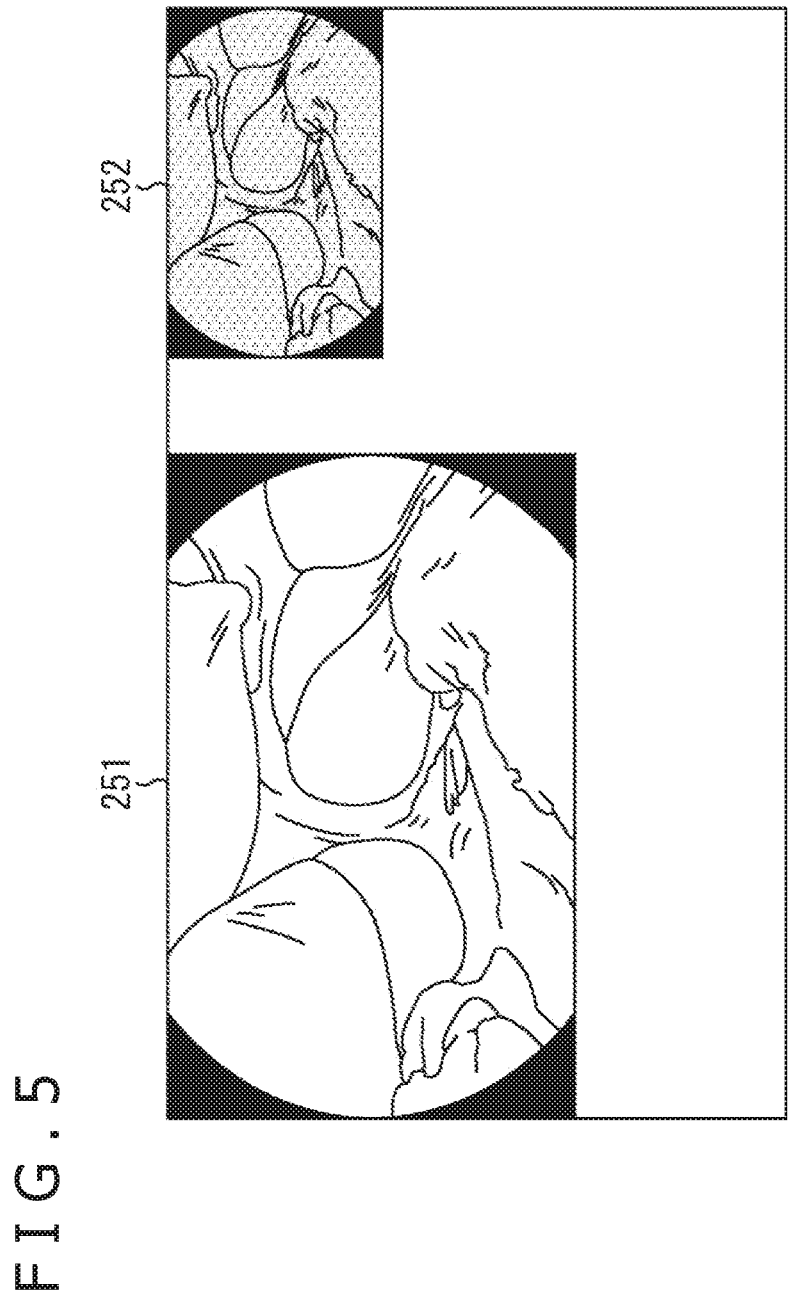
FIG. 5 is a diagram depicting an exemplary display of a pre-update processed image and a post-update processed image.

FIG. 5 depicts a first exemplary display of the pre-update processed image and the post-update processed image.

FIG. 5 depicts the state where a post-update processed image 251 and a pre-update processed image 252 are concurrently displayed on one screen. The post-update processed image 251 displayed in an area at the upper left of the screen is displayed to be larger than the image displayed in an area at the upper right. The operator performing the surgery using the endoscope 101 can thereby easily compare both of the post-update processed image 251 and the pre-update processed image 252 with each other.

In addition, in the example in FIG. 5, the display sizes of the post-update processed image 251 and the pre-update processed image 252 in the screen can be adapted to be adjusted in accordance with the operation of the user (the operator). More specifically, the area having the post-update processed image 251 displayed therein and the area having the pre-update processed image 252 displayed therein are adapted to be exchanged with each other in the screen.

Furthermore, in the example in FIG. 5, in addition to the post-update processed image 251 and the pre-update processed image 252, plural post-update processed images and plural pre-update processed images acquired by varying parameters in each of the image process established after updating the SW and the image process established before updating the SW may be adapted to be displayed.

(Exemplary Display 2)

FIG. 6 depicts a second exemplary display of the pre-update processed image and the post-update processed image.

FIG. 6 depicts the state where the one selected by the user (the operator) of the post-update processed image 251 and the pre-update processed image 252 is displayed. In the example in FIG. 6, the displaying apparatus 202 is adapted to first display thereon the pre-update processed image 252. The user can thereby avoid being embarrassed by the image whose image quality is varied at the time point of the start of the display of the surgical region image. The pre-update processed image 252 and the post-update processed image 251 are thereafter displayed being switched therebetween in accordance with the operation of the user.

In addition, the user interface to switch the display is disposed on the item with which the operator can instantly perform the switching operation at hand, such as the camera head 105 of the endoscope 101 or the surgical implement 117.

(Exemplary Display 3)

Figure 7:
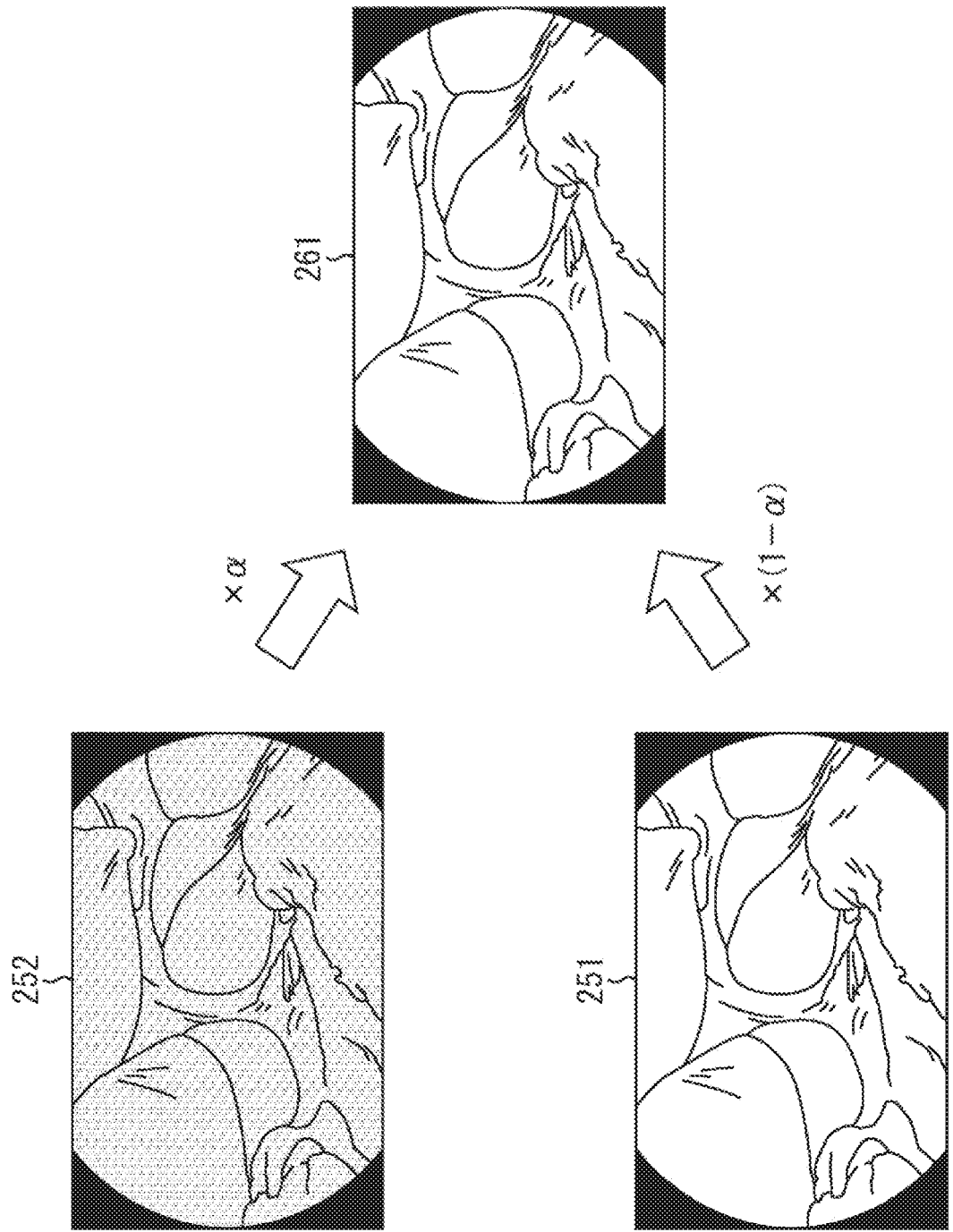
FIG. 7 is a diagram depicting an exemplary display of the pre-update processed image and the post-update processed image.

FIG. 7 depicts a third exemplary display of the post-update processed image and the pre-update processed image.

FIG. 7 depicts the state where the post-update processed image 251 and the pre-update processed image 252 are displayed being added to each other at predetermined ratios for each of the pixels. In the example in FIG. 7, an output image 261 is adapted to be displayed whose pixels each have a pixel value that is the sum of a value acquired by multiplying the pixel value of each of the pixels of the pre-update processed image 252 by a predetermined value $\alpha$ ($\alpha<1$) and a value acquired by multiplying the pixel value of each of the pixels of the post-update processed image 251 by a predetermined value ($1-\alpha$).

In addition, the value $\alpha$ can be adapted to be adjusted by an operation of the user (the operator).

(Exemplary Display 4)

Figure 8:
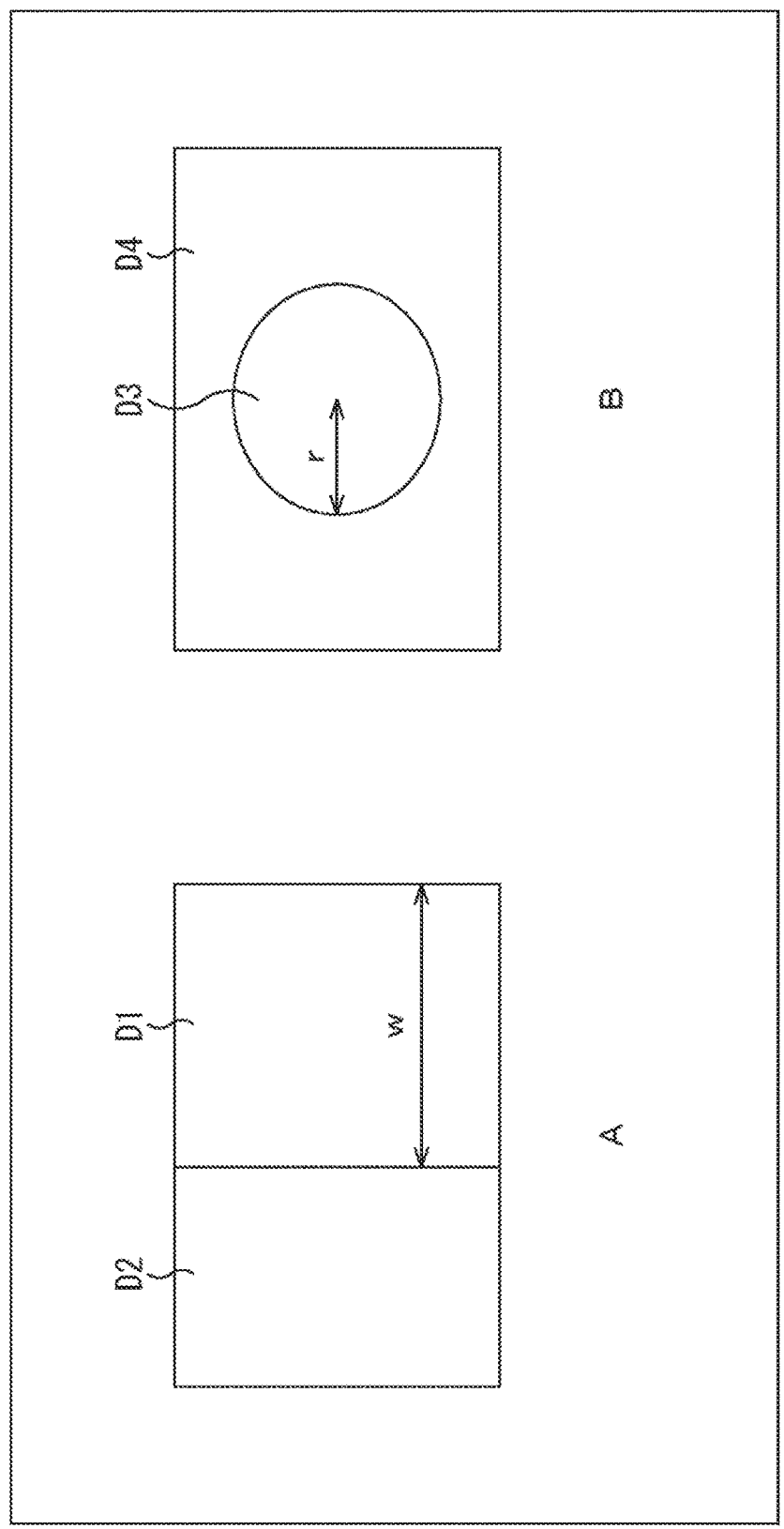
FIG. 8 is a diagram depicting an exemplary display of the pre-update processed image and the post-update processed image.

FIG. 8 depicts a fourth exemplary display of the post-update processed image and the pre-update processed image.

FIG. 8 depicts the state where a first area in the post-update processed image 251 and a second area other than the first area in the pre-update processed image 252 are displayed being synthesized with each other.

In the example in A of FIG. 8, in an area D1 on the right side formed by dividing the screen into areas on the right and the left sides, an image of the portion corresponding to the area D1 in the post-update processed image 251 is first displayed and, in an area D2 on the left side formed by dividing the screen into areas on the right and the left sides, an image of the portion corresponding to the area D2 in the pre-update processed image 252 is displayed. It is assumed that the width w of the area D1, in other words, the border between the area D1 and the area D2 is adjusted by an operation of the user (the operator). Moreover, the images displayed in the area D1 and the area D2 may be adapted to be exchanged with each other by an operation of the user.

Moreover, in the example in B of FIG. 8, in an area including the center of the screen that is, more specifically, a circular area D3 centering the center of the screen, an image of the portion corresponding to the area D3 in the post-update processed image 251 is displayed and, in a peripheral area D4 outside the area D3 in the screen, an image of the portion corresponding to the area D4 in the pre-update processed image 252 is displayed. It is assumed that the radius r of the area D3 that is, in other words, the border between the area D3 and the area D4 is adjusted by an operation of the user (the operator). Moreover, the images displayed in the area D3 and the area D4 may be adapted to be exchanged with each other by an operation of the user. Furthermore, the shape of the area D3 is not limited to the circular shape and may be another shape such as a rectangle.

4. Second Embodiment (Exemplary Configuration of Image Processing Apparatus)

Figure 9:
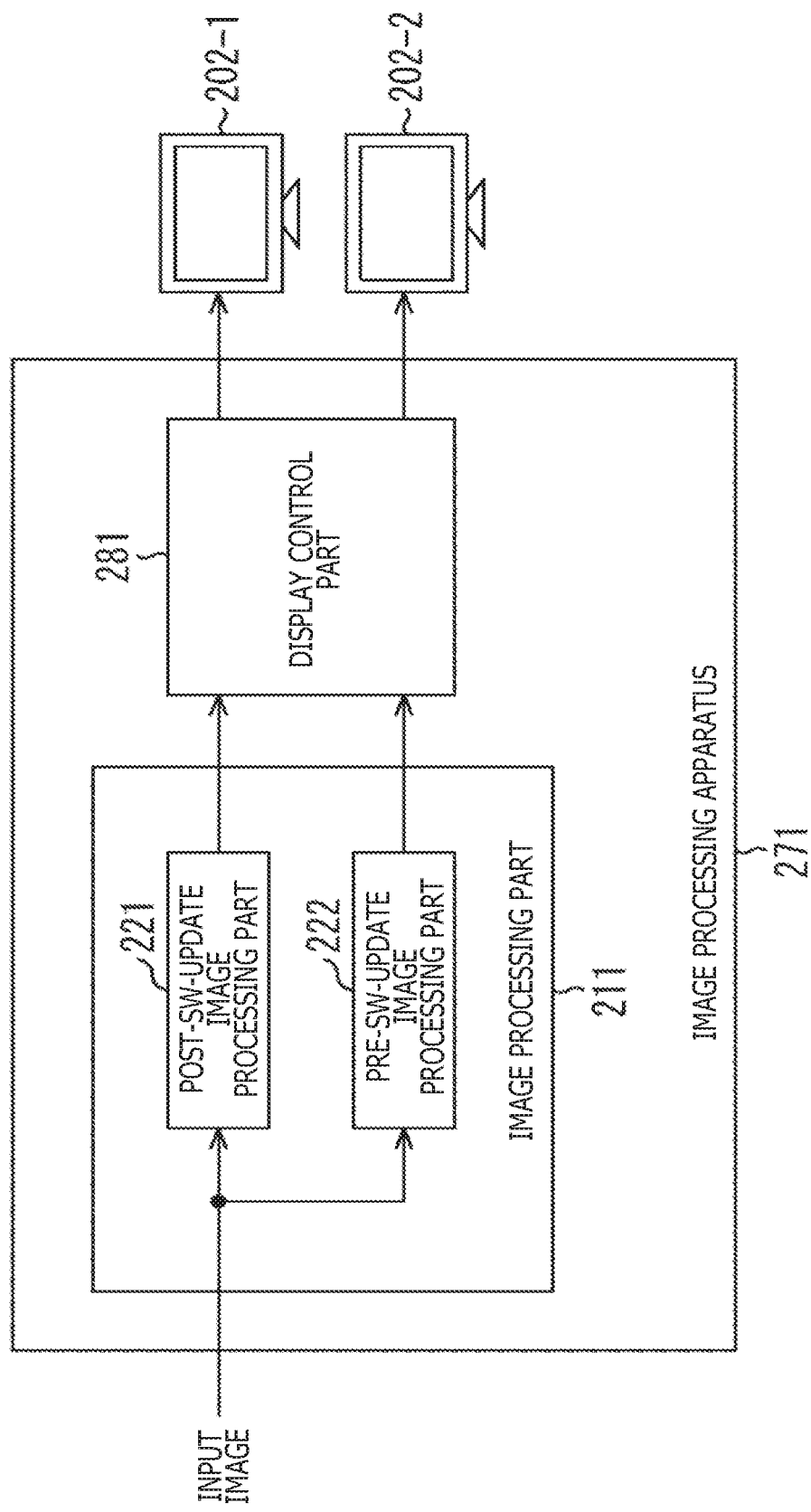
FIG. 9 is a block diagram depicting an exemplary functional configuration of an image processing apparatus of a second embodiment.

FIG. 9 depicts an exemplary configuration of an image processing apparatus of a second embodiment according to the present technique.

The image processing apparatus 271 in FIG. 9 applies the image processes to the image signal of the input image and outputs the result to each of displaying apparatuses 202-1 and 202-2.

The displaying apparatuses 202-1 and 202-2 each display an image on the basis of the image signal input thereinto from the image processing apparatus 201.

The image processing apparatus 271 includes the image processing part 211 and a display control part 281.

In FIG. 9, the image processing part 211 has a configuration same as that depicted in FIG. 3 and will therefore not again be described.

The display control part 281 causes the displaying apparatus 202-1 to display thereon the post-update processed image and causes the displaying apparatus 202-2 to display thereon the pre-update processed image, on the basis of the image signals output from the image processing part 211 (the post-SW-update image processing part 221 and the pre-SW-update image processing part 222).

With such a configuration, the operator performing the surgery using the endoscope 101 can also easily compare these images with each other because the image acquired after the image quality is varied by the update of the SW and the image acquired before the image quality is varied thereby are displayed as the images of the surgical region imaged by the endoscope 101.

5. Third Embodiment (Exemplary Configuration of Image Processing Apparatus)

Figure 10:
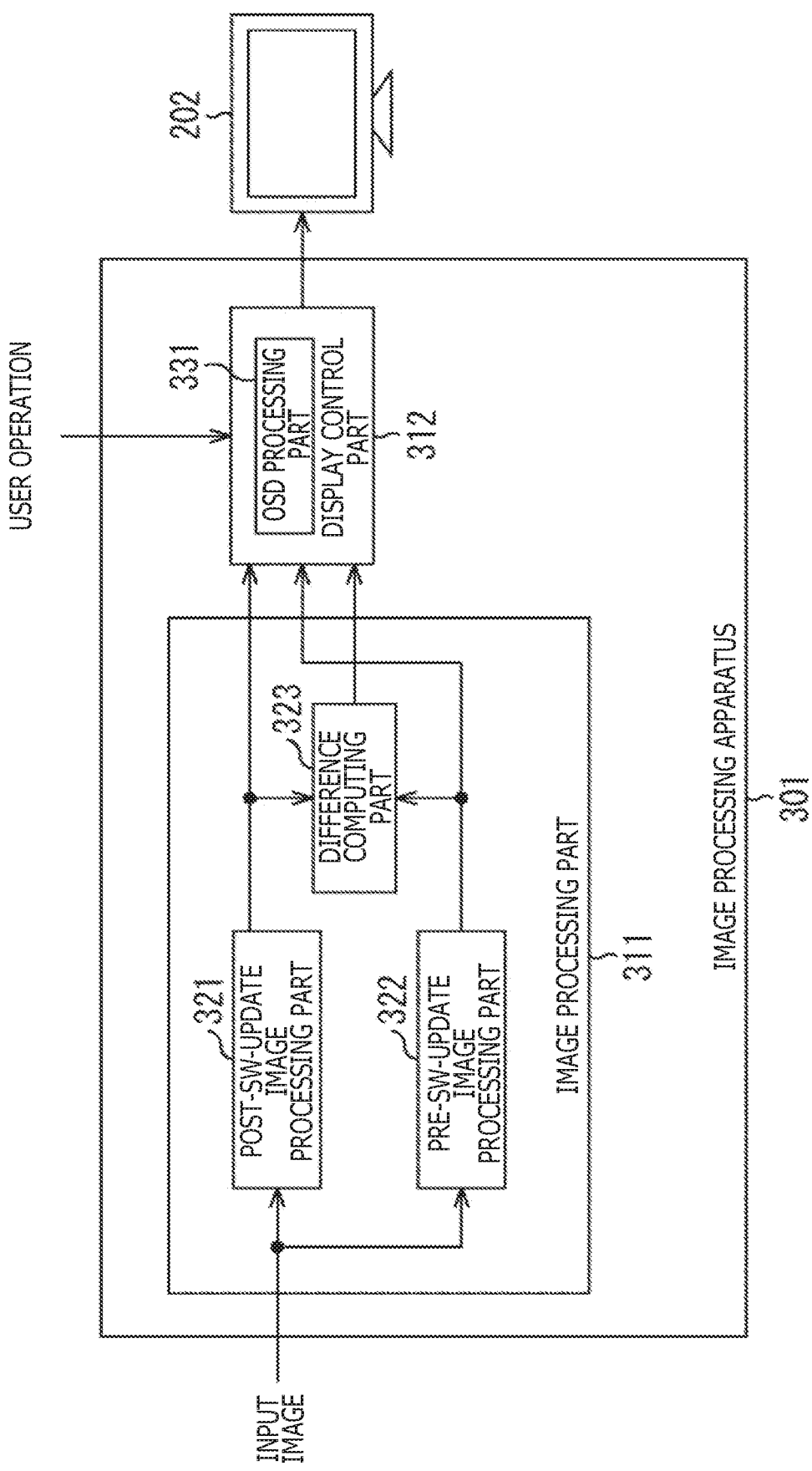
FIG. 10 is a block diagram depicting an exemplary functional configuration of an image processing apparatus of a third embodiment.

FIG. 10 depicts an exemplary configuration of an image processing apparatus of a third embodiment according to the present technique.

The image processing apparatus 301 in FIG. 10 includes an image processing part 311 and a display control part 312.

The image processing part 311 includes a post-SW-update image processing part 321, a pre-SW-update image processing part 322, and a difference computing part 323.

Similar to the post-SW-update image processing part 221 in FIG. 3, the post-SW-update image processing part 321 outputs an image signal of a post-update processed image acquired by applying the image process established after the SW is updated to an input image.

Similar to the pre-SW-update image processing part 222 in FIG. 3, the pre-SW-update image processing part 322 outputs an image signal of a pre-update processed image acquired by applying the image process established before the SW is updated to an input image.

The difference computing part 323 computes the difference between the pre-update processed image and the post-update processed image, and supplies the computation result to the display control part 312.

The display control part 312 causes the displaying apparatus 202 to display thereon at least a portion of at least one of the post-update processed image or the pre-update processed image on the basis of the image signal output from the image processing part 311 (the post-SW-update image processing part 321 and the pre-SW-update image processing part 322).

Moreover, the display control part 312 includes an OSD processing part 331. The OSD processing part 331 OSD-displays the information in accordance with the computation result from the image processing part 311 (the difference computing part 323), in the screen of the displaying apparatus 202.

(Flow of Surgical Region Image Display Process)

Figure 11:
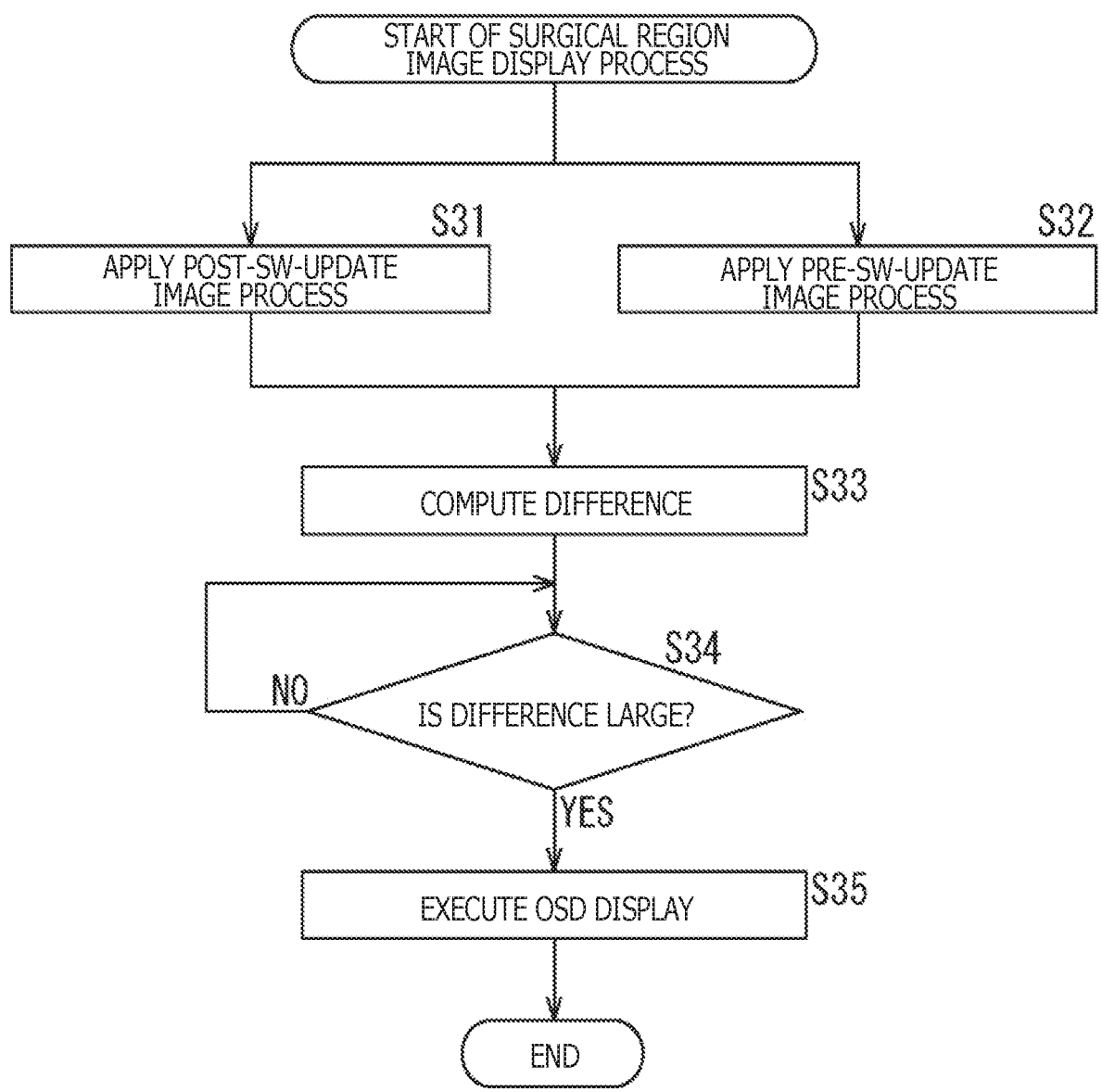
FIG. 11 is a flowchart explaining a surgical region image display process.

A flow of a surgical region image display process executed by the image processing apparatus 301 will next be described with reference to a flowchart in FIG. 11. The process in FIG. 11 are stared when a surgical region image acquired by imaging the surgical region (a moving image) is input into the image processing apparatus 301 from the endoscope 101 (the camera head 105).

At step S31, the post-SW-update image processing part 321 applies the image process established after updating the SW (the image process realized by the SW of the latest version) to the input surgical region image.

At step S32, the pre-SW-update image processing part 322 applies the image process established before updating the SW (the image process realized by the SW of the immediately previous version) to the input surgical region image.

It is assumed that the processes at steps S31 and S32 are concurrently executed in parallel to each other while these processes may serially be executed as described above. The image signal of the post-update processed image to which the image process established after updating the SW is applied and the image signal of the pre-update processed image to which the image process established before updating the SW is applied are output to the display control part 312 and the difference computing part 323.

In addition, at this time, it is assumed that the display control part 312 causes the displaying apparatus 202 to display thereon only the post-update processed image on the basis of the image signal output from the post-SW-update image processing part 321.

At step S33, the difference computing part 323 computes the difference between the pre-update processed image and the post-update processed image. More specifically, the difference computing part 323 calculates the difference in the pixel values of each of the pixels between the pre-update processed image and the post-update processed image, and totals the differences. The computation result is supplied to the display control part 312.

At step S34, the display control part 312 determines whether or not the difference is larger than a predetermined value on the basis of the computation result from the difference computing part 323.

In the case where it is determined that the difference is not larger than the predetermined value, the process at step S34 is repeated and the post-update processed image is continuously displayed on the displaying apparatus 202.

On the other hand, in the case where it is determined that the difference is larger than the predetermined value, the process step advances to step S35.

At step S35, the OSD processing part 331 of the display control part 312 executes an OSD display of information notifying that the difference is larger than the predetermined value. For example, as depicted on the left side of FIG. 12, the OSD processing part 331 OSD-displays a notification image 361 notifying that the difference is larger than the predetermined value, on the post-update processed image displayed on the displaying apparatus 202. The user can thereby recognize the presence of the difference in the image quality between the post-update processed image and the pre-update processed image in the scene that the user currently watches.

In the screen of the displaying apparatus 202, a predetermined operation is thereafter performed by the user such as that for a portion of the notification image 361 to be touched, and a selection screen to select the display mode to compare the post-update processed image and pre-update processed image with each other is adapted to thereby be displayed. As depicted on, for example, the right side of FIG. 12, the display control part 312 displays the selection screen having buttons 381 to 384 disposed therein to select any of four display modes. In each of the four display modes, for example, the display described in each of the Exemplary Display 1 to Exemplary Display 4 described above is executed.

According to the above processes, in the case where the difference is large between the image acquired after the image quality is varied by the update of the SW and the image acquired before the image quality is varied thereby, the operator performing the surgery using the endoscope 101 can cause these images to be displayed each in a desired display form to easily compare these images with each other.

6. Fourth Embodiment (Exemplary Configuration of Image Processing Apparatus)

Figure 13:
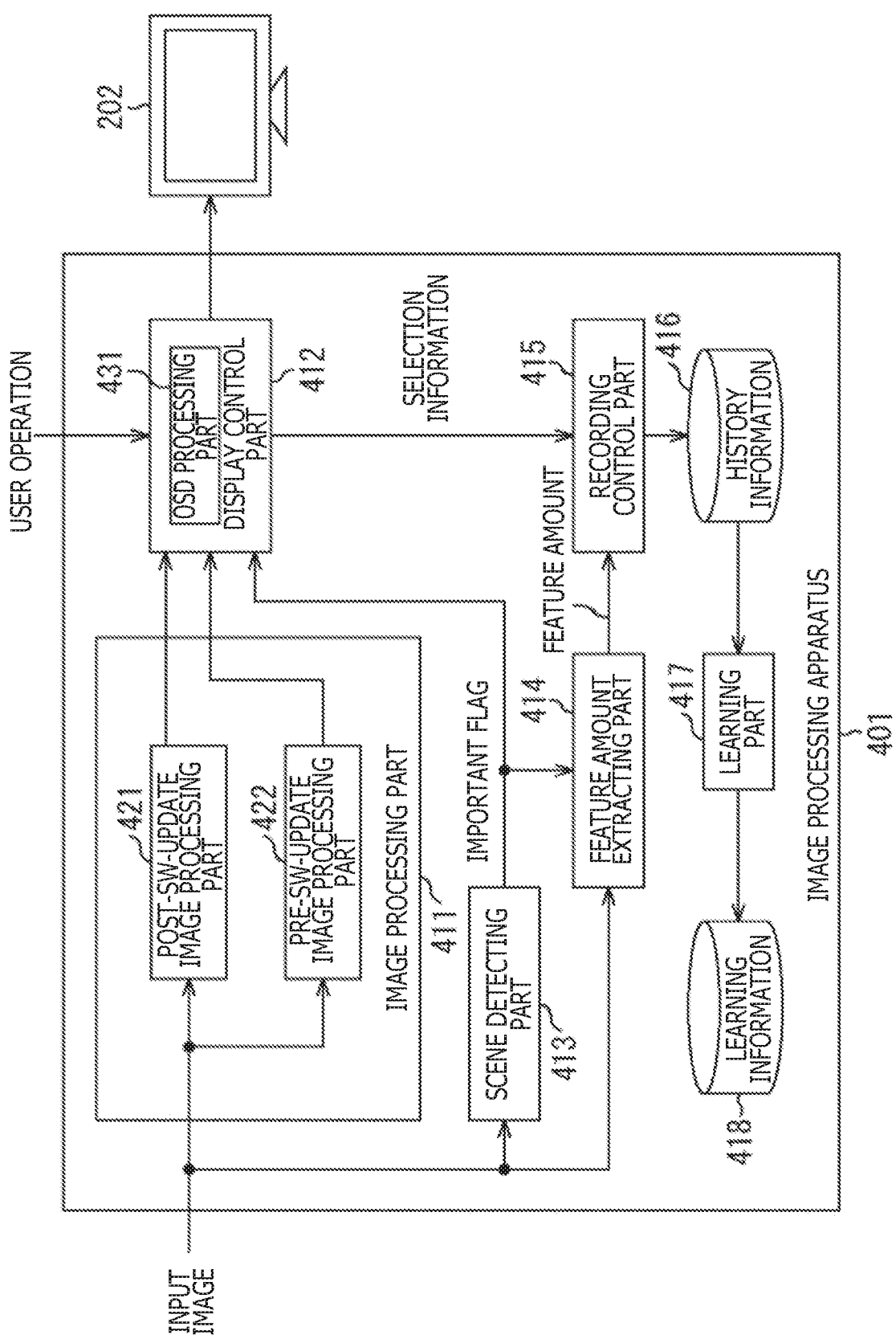
FIG. 13 is a block diagram depicting an exemplary functional configuration of an image processing apparatus of a fourth embodiment.

FIG. 13 depicts an exemplary configuration of an image processing apparatus of a fourth embodiment according to the present technique.

The image processing apparatus 401 in FIG. 13 includes an image processing part 411, a display control part 412, a scene detecting part 413, a feature amount extracting part 414, a recording control part 415, a history information recording part 416, a learning part 417, and a learning information recording part 418.

The image processing part 411 includes a post-SW-update image processing part 421 and a pre-SW-update image processing part 422.

Similar to the post-SW-update image processing part 221 in FIG. 3, the post-SW-update image processing part 421 outputs an image signal of a post-update processed image acquired by applying the image process established after the SW is updated, to the input image.

Similar to the pre-SW-update image processing part 222 in FIG. 3, the pre-SW-update image processing part 422 outputs an image signal of a pre-update processed image acquired by applying the image process established before the SW is updated, to the input image.

The display control part 412 causes the displaying apparatus 202 to display thereon the one selected by the user of the post-update processed image and the pre-update processed image on the basis of the image signal output from the image processing part 411 (the post-SW-update image processing part 421 and the pre-SW-update image processing part 422).

Moreover, the display control part 412 includes an OSD processing part 431. The OSD processing part 431 OSD-displays the information in accordance with an importance flag from the scene detecting part 413 described later, in the screen of the displaying apparatus 202.

The scene detecting part 413 detects a scene with a high importance degree in the input image. In the case where the scene detecting part 413 detects a scene with a high importance degree, the scene detecting part 413 supplies the importance flag that indicates that this scene is a scene with a high importance degree, to the display control part 412 and the feature amount extracting part 414.

The feature amount extracting part 414 extracts the feature amount of the scene with a high importance degree detected in the input image on the basis of the importance flag from the scene detecting part 413, and supplies this feature amount to the recording control part 415.

The recording control part 415 correlates the feature amount from the feature amount extracting part 414 and the selection information from the display control part 412 with each other and records these in the history information recording part 416 as history information. The selection information is information that indicates which one of the post-update processed image and the pre-update processed image is selected by the user for the scene with a high importance degree detected in the input image.

The learning part 417 learns which one of the post-update processed image and the pre-update processed image is selected by the user for the scene with a high importance degree detected in the input image for each feature amount on the basis of the history information recorded in the history information recording part 416. The learning result acquired by the learning is recorded in the learning information recording part 418.

(Flow of Surgical Region Image Display Process)

Figure 14:
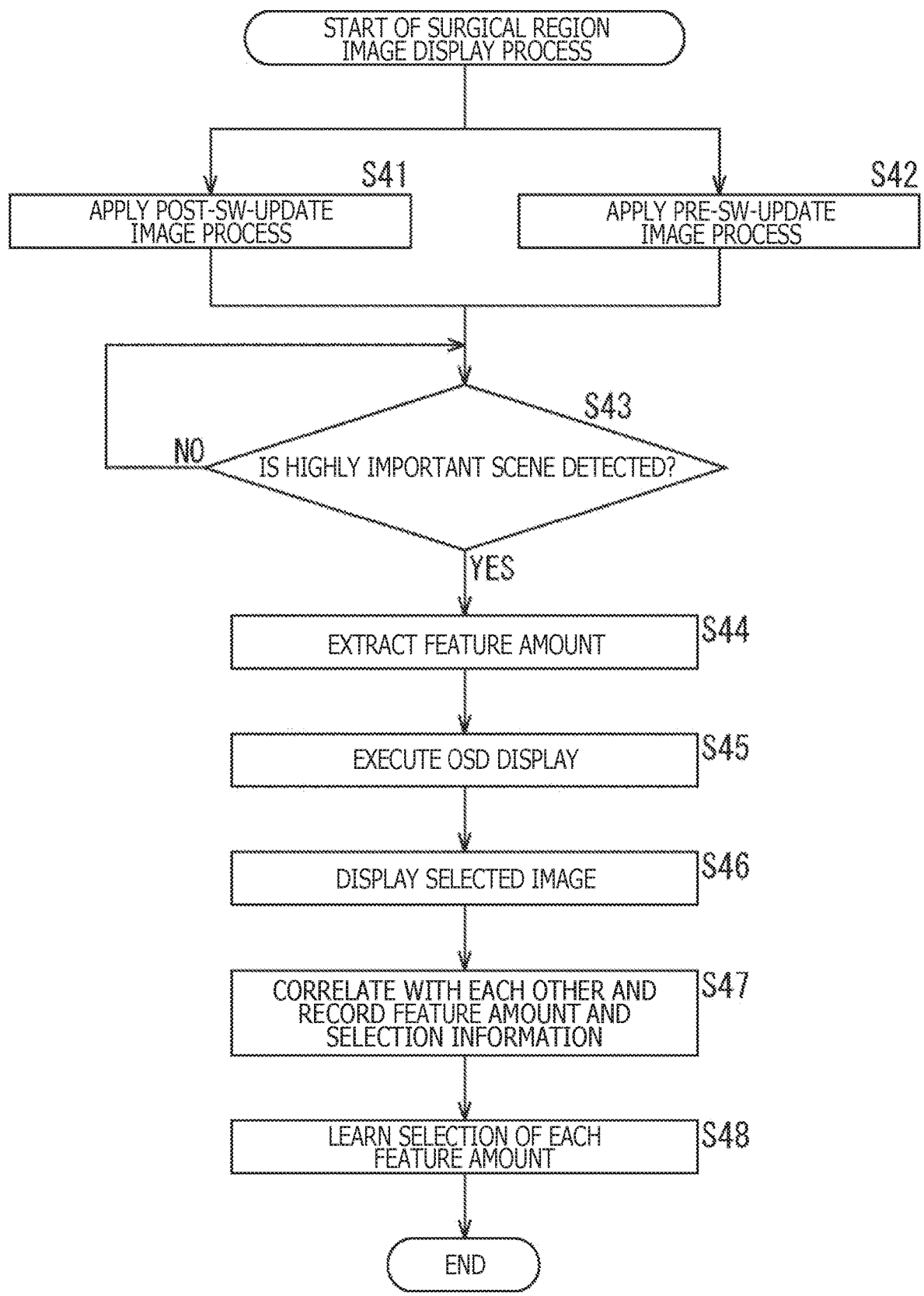
FIG. 14 is a flowchart explaining the surgical region image display process.

A flow of a surgical region image display process executed by the image processing apparatus 401 will next be described with reference to a flowchart in FIG. 14. The processes in FIG. 14 are stared when a surgical region image acquired by imaging the surgical region (a moving image) is input into the image processing apparatus 401 from the endoscope 101 (the camera head 105).

At step S41, the post-SW-update image processing part 421 applies the image process established after updating the SW (the image process realized by the SW of the latest version) to the input image.

At step S42, the pre-SW-update image processing part 422 applies the image process established before updating the SW (the image process realized by the SW of the immediately previous version) to the input image.

It is assumed that the processes at steps S41 and S42 are concurrently executed in parallel to each other while these processes may serially be executed as described above. The image signal of the post-update processed image to which the image process established after updating the SW is applied and the image signal of the pre-update processed image to which the image process established before updating the SW is applied are output to the display control part 412.

In addition, at this time, it is assumed that the display control part 412 causes the displaying apparatus 202 to display thereon both of the post-update processed image and the pre-update processed image on the basis of the image signals output from the image processing part 411.

At step S43, the scene detecting part 413 determines whether or not the scene detecting part 413 detects any scene with a high importance degree in the input image. The scene with a high importance degree is defined as, for example, a scene in which an incision, peeling off, or the like of a tissue is performed, and these are detected on the basis of the shapes of the surgical implements, the color of the surgical region, and the like depicted in the input image (the surgical region image).

In the case where the scene detecting part 413 determines that no scene with any high importance degree is detected, the process at step S43 is repeated and both of the post-update processed image and the pre-update processed image are continuously displayed on the displaying apparatus 202.

On the other hand, in the case where the scene detecting part 413 determines that a scene with a high importance degree is detected, the scene detecting part 413 supplies the importance flag to the display control part 412 and the feature amount extracting part 414, and the process step advances to step S44.

At step S44, the feature amount extracting part 414 extracts the feature amount of the scene with a high importance degree detected in the input image on the basis of the importance flag from the scene detecting part 413, and supplies this feature amount to the recording control part 415. The feature amount of the scene with a high importance degree is defined as information in accordance with the shapes of the surgical implements, the color of the surgical region, and the like that are employed as the criteria for detecting the scene.

At step S45, the OSD processing part 431 of the display control part 412 executes an OSD display of information indicating that the scene displayed at this time is the scene with a high importance degree on the basis of the importance flag from the scene detecting part 413.

In addition, the processes at step S44 and step S45 may also be executed in parallel to each other.

When the OSD display is executed, the image processing apparatus 401 next causes the user to select which one of the pre-update processed image and the post-update processed image to be displayed. When either the pre-update processed image or the post-update processed image is selected by the user, the process step advances to step S46.

At step S46, the display control part 412 causes the displaying apparatus 202 to display only the one selected by the user of the pre-update processed image and the post-update processed image. At this time, the display control part 412 supplies selection information indicating the one selected by the user of the pre-update processed image and the post-update processed image (the one displayed on the displaying apparatus 202) to the recording control part 415.

At step S47, the recording control part 415 correlates the feature amount from the feature amount extracting part 414 and the selection information from the display control part 412 with each other and records these in the history information recording part 416 as history information.

At step S48, the learning part 417 learns which one of the post-update processed image and the pre-update processed image is selected by the user for the scene with a high importance degree detected in the input image, for each feature amount on the basis of the history information recorded in the history information recording part 416. In this case, it is learned using machine learning that which one of the post-update processed image and the pre-update processed image is more often selected by the user for each feature amount.

According to the above processes, the operator performing a surgery using the endoscope 101 can easily compare the image acquired after the image quality is varied by the update of the SW and the image acquired before the image quality is varied thereby to select the more advantageous one to cause this one to be displayed. Moreover, it can be learned that which display form of those of the image acquired after the image quality is varied by the update of the SW and the image acquired before the image quality is varied thereby is more advantageous for the operator for the scene with a high importance degree.

7. Fifth Embodiment (Exemplary Configuration of Image Processing Apparatus)

Figure 15:
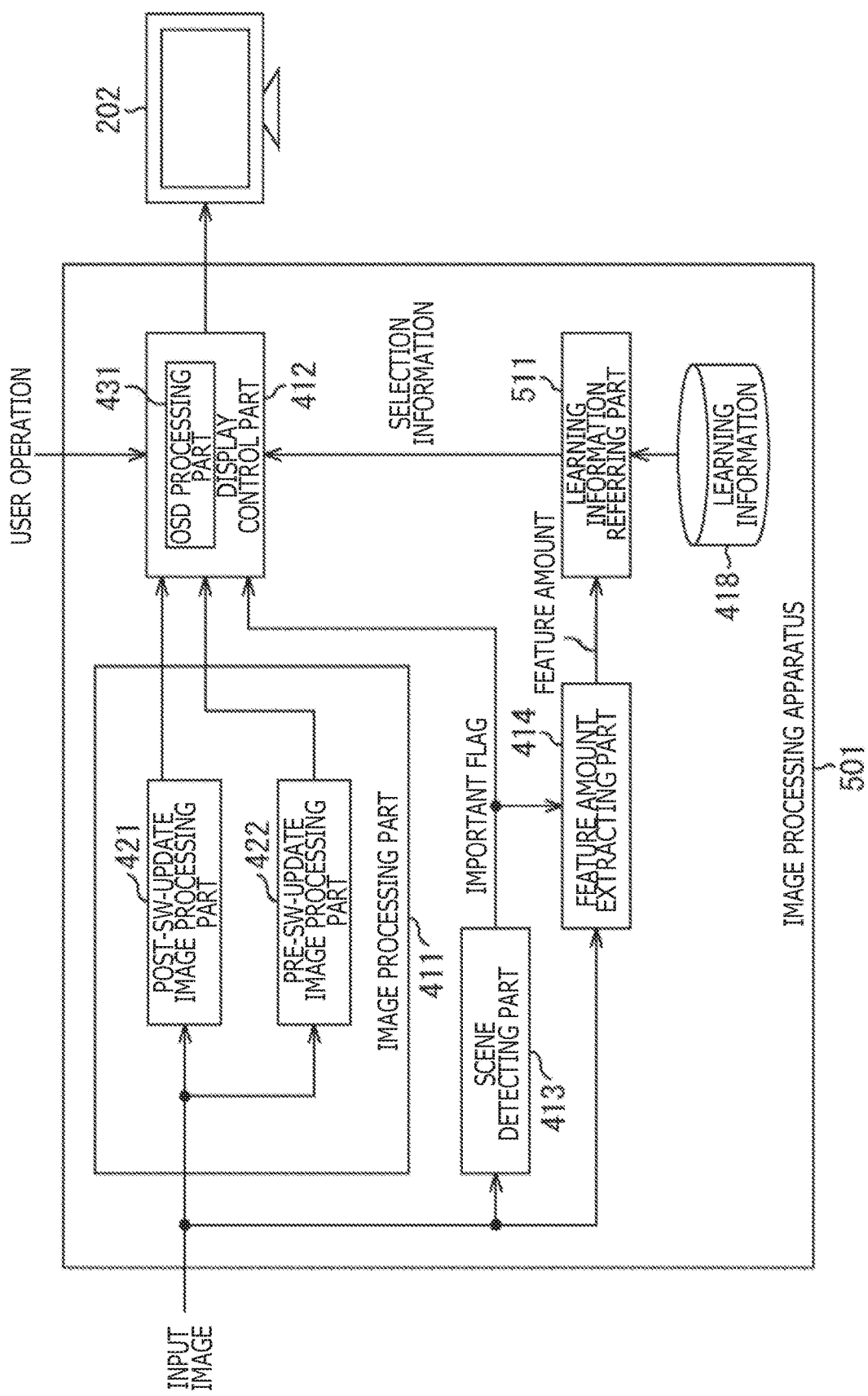
FIG. 15 is a block diagram depicting an exemplary functional configuration of an image processing apparatus of a fifth embodiment.

FIG. 15 depicts an exemplary configuration of an image processing apparatus of a fifth embodiment according to the present technique.

The image processing apparatus 501 in FIG. 15 automatically selects the more advantageous one for the operator of the post-update processed image and the pre-update processed image and causes this image to be displayed, for the scene with a high importance degree in a newly input surgical region image, using the above learning result.

The image processing apparatus 501 includes the image processing part 411, the display control part 412, the scene detecting part 413, the feature amount extracting part 414, the learning information recording part 418, and a learning information referring part 511.

In FIG. 15, the image processing part 411, the display control part 412, the scene detecting part 413, the feature amount extracting part 414, and the learning information recording part 418 are respectively same as the configurations depicted in FIG. 13 and will therefore not again be described.

The learning information referring part 511 refers to the learning information that corresponds to the feature amount of the scene with a high importance degree detected in the input image that is newly input, from the learning information recorded in the learning information recording part 418. On the basis of the referred learning information, the learning information referring part 511 supplies the selection information correlated with the feature amount, to the display control part 412.

(Flow of Surgical Region Image Display Process)

A flow of the surgical region image display process executed by the image processing apparatus 501 will next be described with reference to a flowchart in FIG. 16. The processes in FIG. 16 are started when a surgical region image acquired by imaging the surgical region (a moving image) is input into the image processing apparatus 501 from the endoscope 101 (the camera head 105).

Figure 16:
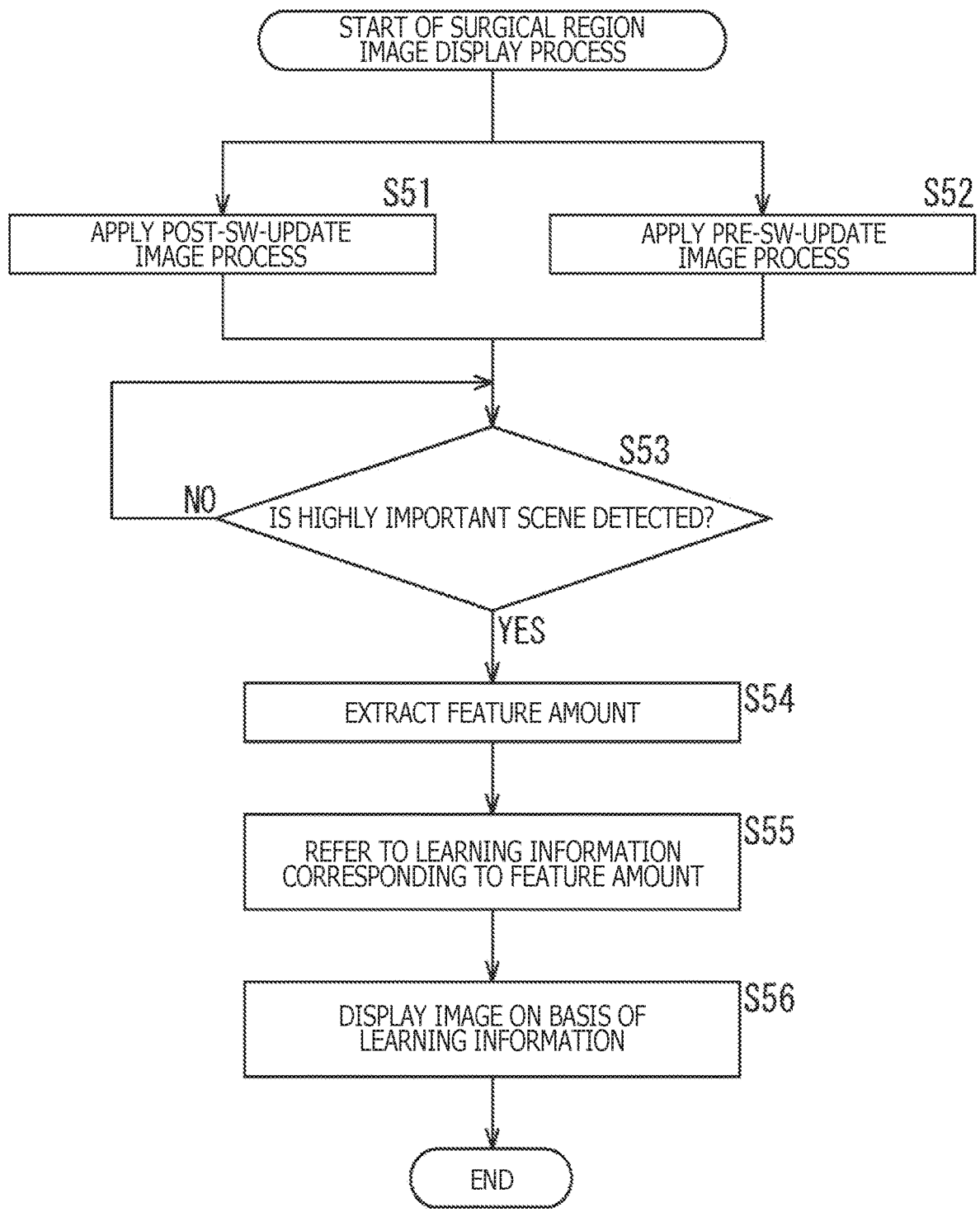
FIG. 16 is a flowchart explaining a surgical region image display process.

In addition, processes at steps S51 to S54 in FIG. 16 are basically similar to the processes at steps S41 to S44 in FIG. 15 and will therefore not again be described.

At step S54, when the feature amount of the scene with a high importance degree detected in the input image is extracted, the feature amount is supplied to the learning information referring part 511.

At step S55, the learning information referring part 511 refers to the learning information that corresponds to the feature amount from the feature amount extracting part 414, from the learning information recorded in the learning information recording part 418. The learning information referring part 511 supplies the selection information correlated with the feature amount from the feature amount extracting part 414, to the display control part 412 on the basis of the referred learning information.

At step S56, the display control part 412 causes the displaying apparatus 202 to display thereon only the one indicated by the selection information of the post-update processed image and the pre-update processed image, on the basis of the selection information from the learning information referring part 511.

According to the above processes, the more advantageous one for the operator can be displayed of the image acquired after the image quality is varied by the update of the SW and the image acquired before the image quality is varied thereby on the basis of the learning result, for the scene with a high importance degree.

The example where the technique according to the present disclosure is applied to the endoscopic surgery system has been described in the above while the system to which the technique according to the present disclosure is applicable is not limited to the above example. For example, the technique according to the present disclosure may be applied to an inspective flexible endoscope system and a microscopic surgery system.

Moreover, the embodiments of the present technique are not limited to the above embodiments and various changes can be made thereto within the scope not departing from the gist of the present technique.

Furthermore, the present technique can take the following configurations.

(1)

A surgical image processing apparatus including:
an image processing part that applies an image process by software to a surgical region image; and
a display control part that controls a display of the surgical region image to which the image process is applied, in which
the image processing part produces a pre-update processed image acquired by applying the image process established before updating the software to the surgical region image and a post-update processed image acquired by applying the image process established after updating the software to the surgical region image, and the display control part controls a display of at least a portion of at least either one of the pre-update processed image or the post-update processed image.

(2)

The surgical image processing apparatus according to the above (1), in which the image processing part executes the image process established before updating the software and the image process established after the software updating, in parallel to each other.

(3)

The surgical image processing apparatus according to the above (1) or (2), in which the display control part causes the pre-update processed image and the post-update processed image to be concurrently displayed in one screen.

(4)

The surgical image processing apparatus according to the above (3), in which the display control part adjusts display sizes of the pre-update processed image and the post-update processed image in the screen in accordance with an operation of a user.

(5)

The surgical image processing apparatus according to the above (1) or (2), in which the display control part causes the pre-update processed image and the post-update processed image to be displayed on different display apparatuses.

(6)

The surgical image processing apparatus according to the above (1) or (2), in which the display control part causes one selected by a user, of the pre-update processed image and the post-update processed image, to be displayed.

(7)

The surgical image processing apparatus according to the above (1) or (2), in which the display control part adds the pre-update processed image and the post-update processed image to each other at predetermined ratios for each pixel, to be displayed.

(8)

The surgical image processing apparatus according to the above (1) or (2), in which the display control part synthesizes a first area of the pre-update processed image and a second area other than the first area of the post-update processed image with each other, to be displayed.

(9)

The surgical image processing apparatus according to the above (8), in which the first area is one area formed by dividing a screen into two on left and right sides, and the second area is the other area formed by dividing the screen into two on the left and right sides.

(10)

The surgical image processing apparatus according to the above (8), in which the first area is a central area that includes the center of a screen, and the second area is a peripheral area outside the central area in the screen.

(11)

The surgical image processing apparatus according to any of the above (8) to (10), in which a border between the first area and the second area is determined by an operation of a user.

(12)

The surgical image processing apparatus according to the above (1) or (2), further including a difference computing part that computes a difference between the pre-update processed image and the post-update processed image, in which in the case where the difference is larger than a predetermined value, the display control part controls a display of information notifying of the case.

(13)

The surgical image processing apparatus according to the above (1) or (2), further including a scene detecting part that detects a predetermined scene in the image, in which the display control part causes one selected by a user, of the pre-update processed image and the post-update processed image, to be displayed for the detected scene.

(14)

The surgical image processing apparatus according to the above (13), further including a feature amount extracting part that extracts a feature amount of the detected scene, and a recording control part that correlates the extracted feature amount and selection information indicating the one selected by the user, of the pre-update processed image and the post-update processed image, for the detected scene with each other and records the extracted feature amount and the selection information therein as history information.

(15)

The surgical image processing apparatus according to the above (14), further including a learning part that learns which one of the pre-update processed image and the post-update processed image is selected by the user for the detected scene for each feature amount of the scene on the basis of the history information.

(16)

The surgical image processing apparatus according to the above (15), further including a referring part that refers to a learning result corresponding to the feature amount of a predetermined scene detected in another image, in which the display control part causes either the pre-update processed image or the post-update processed image to be displayed for the predetermined scene in the other image on the basis of the referred learning result.

(17)

An image processing method executed by a surgical image processing apparatus that includes an image processing part that applies an image process by software to a surgical region image, and a display control part that controls a display of the surgical region image to which the image process is applied, the method including steps of:

producing a pre-update processed image acquired by applying the image process established before updating the software to the surgical region image and a post-update processed image acquired by applying the image process established after updating the software to the surgical region image; and controlling a display of at least a portion of at least either one of the pre-update processed image or the post-update processed image.

(18)

A surgery system including:
a surgical imaging apparatus that acquires a surgical region image; and
a surgical image processing apparatus that includes
an image processing part that applies an image process by software to the surgical region image; and
a display control part that controls a display of the surgical region image to which the image process is applied, in which
the image processing part produces a pre-update processed image acquired by applying the image process established before updating the software to the surgical region image and a post-update processed image acquired by applying the image process established after updating the software to the surgical region image, and
the display control part controls a display of at least a portion of at least either one of the pre-update processed image or the post-update processed image.

REFERENCE SIGNS LIST

201 Image processing apparatus, 211 Image processing part, 212 Display control part, 221 Post-SW-update image processing part, 222 Pre-SW-update image processing part, 281 Display control part, 301 Image processing apparatus, 311 Image processing part, 312 Display control part, 321 Post-SW-update image processing part, 322 Pre-SW-update image processing part, 323 Difference computing part, 331 OSD processing part, 401 Image processing apparatus, 411 Image processing part, 412 Display control part, 413 Scene detecting part, 414 Feature amount extracting part, 415 Recording control part, 416 History information recording part, 417 Learning part, 418 Learning information recording part, 421 Post-SW-update image processing part, 422 Pre-SW-update image processing part, 431 OSD processing part, 511 Learning information referring part

The invention claimed is:

1. A surgical image processing apparatus comprising:
image processing circuitry configured to apply an image process by software to a surgical region image;
display control circuitry configured to control a display of the surgical region image to which the image process is applied; and
scene detecting circuitry configured to detect a scene and determine whether the detected scene is a predetermined scene in the surgical region image, wherein
the image processing circuitry is configured to produce a pre-update processed image acquired by applying the image process established before updating the software to the surgical region image and a post-update processed image acquired by applying the image process established after updating the software to the surgical region image, and
the display control circuitry is configured to
control display of at least a portion of at least either one of the pre-update processed image or the post-update processed image,
add the pre-update processed image and the post-update processed image to each other at predetermined ratios for each pixel, such that each pixel includes both the pre-update processed image and the post-update processed image, and
on condition that the detected scene is the predetermined scene, cause one selected by a user, of the pre-update processed image and the post-update processed image, to be displayed for the detected scene.

2. The surgical image processing apparatus according to claim 1, wherein
the image processing circuitry is configured to execute the image process established before updating the software and the image process established after the software updating, in parallel to each other.

3. The surgical image processing apparatus according to claim 1, wherein
the display control circuitry is configured to cause the pre-update processed image and the post-update processed image to be displayed on different displaying apparatuses.

4. The surgical image processing apparatus according to claim 1, further comprising:
difference computing circuitry configured to compute a difference between the pre-update processed image and the post-update processed image, wherein
in a case where the difference is larger than a predetermined value, the difference computing circuitry is configured to output notification of the case.

5. The surgical image processing apparatus according to claim 1, wherein
the display control circuitry is configured to cause the pre-update processed image and the post-update processed image to be concurrently displayed in one screen.

6. The surgical image processing apparatus according to claim 5, wherein
the display control circuitry is configured to adjust display sizes of the pre-update processed image and the post-update processed image in the screen in accordance with an operation of a user.

7. The surgical image processing apparatus according to claim 1, wherein
the display control circuitry is configured to synthesize a first area of the pre-update processed image and a second area other than the first area of the post-update processed image with each other, to be displayed.

8. The surgical image processing apparatus according to claim 7, wherein
the first area is one area formed by dividing a screen into two on left and right sides, and
the second area is another area formed by dividing the screen into two on the left and right sides.

9. The surgical image processing apparatus according to claim 7, wherein
the first area is a central area that includes a center of a screen, and
the second area is a peripheral area outside the central area in the screen.

10. The surgical image processing apparatus according to claim 7, wherein
a border between the first area and the second area is determined by an operation of a user.

11. The surgical image processing apparatus according to claim 1, further comprising:
feature extracting circuitry configured to extract a feature amount of the detected scene; and
recording control circuitry configured to correlate the extracted feature amount and selection information indicating the one selected by the user, of the pre-update processed image and the post-update processed image, for the detected scene with each other and record the extracted feature amount and the selection information therein as history information.

12. The surgical image processing apparatus according to claim 11, further comprising:
 learning circuitry configured to learn which one of the pre-update processed image and the post-update processed image is selected by the user for the detected scene for each feature amount of the scene on a basis of the history information.

13. The surgical image processing apparatus according to claim 12, further comprising:
 referring circuitry configured to refer to a learning result corresponding to the feature amount of a predetermined scene detected in another image, wherein
 the display control circuitry is configured to cause either the pre-update processed image or the post-update processed image to be displayed for the predetermined scene in the other image on a basis of the referred learning result.

14. An image processing method, the method comprising:
 producing a pre-update processed image by applying an image process established before updating software to a surgical region image and a post-update processed image by applying the image process established after updating the software to the surgical region image;
 controlling a display of at least a portion of at least either one of the pre-update processed image or the post-update processed image; and
 adding the pre-update processed image and the post-update processed image to each other at predetermined ratios for each pixel, such that each pixel includes both the pre-update processed image and the post-update processed image;
 determining whether a detected scene is a predetermined scene in the surgical region image; and
 on condition that the detected scene is the predetermined scene, causing one selected by a user, of the pre-update processed image and the post-update processed image, to be displayed for the detected scene.

15. The image processing method according to claim 14, further comprising:
 computing a difference between the pre-update processed image and the post-update processed image, wherein
 in a case where the difference is larger than a predetermined value, outputting notification of the case.

16. A surgery system comprising:
 a surgical imager that acquires a surgical region image; and
 a surgical image processor that includes
  image processing circuitry configured to image process by software to the surgical region image;
 display control circuitry configured to control a display of the surgical region image to which the image process is applied; and
  scene detecting circuitry configured to detect a predetermined scene in the surgical region image and determine whether the detected scene is a predetermined scene in the surgical region image, wherein
  the image processing circuitry is configured to produce a pre-update processed image acquired by applying the image process established before updating the software to the surgical region image and a post-update processed image acquired by applying the image process established after updating the software to the surgical region image, and
  the display control circuitry is configured to
   control display of at least a portion of at least either one of the pre-update processed image or the post-update processed image,
   add the pre-update processed image and the post-update processed image to each other at predetermined ratios for each pixel, such that each pixel includes both the pre-update processed image and the post-update processed image, and
   on condition that the detected scene is the predetermined scene, cause one selected by a user, of the pre-update processed image and the post-update processed image, to be displayed for the detected scene.

17. The surgery system according to claim 16, further comprising:
 difference computing circuitry configured to compute a difference between the pre-update processed image and the post-update processed image, wherein
 in a case where the difference is larger than a predetermined value, the difference computing circuitry is configured to output notification of the case.

* * * * *